(12) United States Patent
Morris et al.

(10) Patent No.: US 8,142,722 B2
(45) Date of Patent: Mar. 27, 2012

(54) TEST ELEMENT AND TESTER FOR ANALYZING SOLUTIONS

(75) Inventors: David Alexander Nathaniel Morris, Granger, IN (US); Teresa Lynn Swanson, Elkhart, IN (US)

(73) Assignee: Hach Company, Loveland, CO (US)

( * ) Notice: Subject to any disclaimer, the term of this patent is extended or adjusted under 35 U.S.C. 154(b) by 775 days.

(21) Appl. No.: 11/835,567

(22) Filed: Aug. 8, 2007

(65) Prior Publication Data

US 2007/0287182 A1    Dec. 13, 2007

Related U.S. Application Data

(63) Continuation-in-part of application No. 11/623,199, filed on Jan. 15, 2007.

(60) Provisional application No. 60/836,322, filed on Aug. 8, 2006.

(51) Int. Cl.
*G01N 1/10* (2006.01)

(52) U.S. Cl. ............... 422/82.05; 422/68.1; 422/82.09; 356/446; 356/246; 436/95; 436/164; 436/180

(58) Field of Classification Search ............... None
See application file for complete search history.

(56) References Cited

U.S. PATENT DOCUMENTS

| | | | |
|---|---|---|---|
| 5,049,487 A | 9/1991 | Phillips et al. | |
| 5,304,468 A | 4/1994 | Phillips et al. | |
| 5,780,304 A | 7/1998 | Matzinger et al. | |
| 5,965,456 A | 10/1999 | Malmqvist et al. | |
| 5,965,458 A | 10/1999 | Kouvonen et al. | |
| 6,030,842 A | 2/2000 | Peachey-Stoner | |
| 6,285,454 B1 * | 9/2001 | Douglas et al. | 356/446 |
| 6,544,475 B1 * | 4/2003 | Douglas et al. | 422/61 |
| 6,602,469 B1 | 8/2003 | Maus et al. | |
| 6,979,571 B2 | 12/2005 | Modzelewski et al. | |
| 6,986,999 B2 | 1/2006 | Christner et al. | |
| 2006/0110283 A1 * | 5/2006 | Fish | 422/52 |

* cited by examiner

*Primary Examiner* — Sally Sakelaris
(74) *Attorney, Agent, or Firm* — David G. Maire; Beusse Wolter Sanks Mora & Maire, P.A.

(57) ABSTRACT

An apparatus for analyzing an aqueous solution, as may be implemented with a hand-held portable electronic device (10) and test element (16). A test pad (32) of the test element responsive in color to a characteristic of an aqueous solution is interrogated by the device by measuring intensity values of an interrogating test light as reflected off of the test pad. The test pad may be supported on an opaque and non-reflective substrate (28) that cooperates with an opaque edge portion (14E) of a test element placement member (14B) and associated side walls (14W) of the device to minimize the impingement of ambient light onto the test pad during interrogation.

18 Claims, 14 Drawing Sheets

TEST ELEMENT AND TESTER FOR ANALYZING SOLUTIONS

CROSS-REFERENCE TO RELATED APPLICATIONS

This application is a continuation-in-part and claims priority to and benefit of the 15 Jan. 2007 filing date of U.S. patent application Ser. No. 11/623,199, and it also claims priority to and benefit of the 8 Aug. 2006 filing date of U.S. provisional patent application 60/836,322. The full disclosure of both of these previous applications is incorporated herein by reference.

FIELD OF THE INVENTION

The present invention relates generally to analyzing solutions to determine concentrations of constituent solutes, and more specifically to a method and apparatus for determining one or more characteristics of an aqueous solution, and in one embodiment to a portable, hand-held, self-calibrating electronic device and associated test element for determining chemical characteristics of pool or spa water.

BACKGROUND OF THE INVENTION

Test elements for analyzing aqueous solutions are generally known. For example, test elements for analyzing pool or spa water typically include three chemically treated pads arranged on a substrate; one for measuring free chlorine or bromine concentration, one for measuring pH level and one for measuring total alkalinity of the pool or spa water. To analyze the pool or spa water, such a test element is typically exposed to the pool or spa water, and a chemical reaction then takes place between the chemicals on each of the pads and the pool or spa water. This causes each of the pads to change to a color that is indicative of the corresponding pool or spa water characteristic. The colors of the pads are then typically compared visually to a color chart that maps pad color to a corresponding pool or spa water characteristic.

Test elements are also known for analyzing blood and urine samples. U.S. Pat. No. 5,304,468 describes a test strip and apparatus for determining blood glucose levels by measuring the reflectance of the test strip. The test strip is placed in a detector and a removable cover is then closed to shield the assembly from ambient light. The test strip is illuminated by an LED and the reflectance is measured and correlated to a blood glucose level. The device is calibrated for variations in LED brightness by placing the test into the device prior to it being wetted with blood, and adjusting power to the LED if the reflectance is different than a predetermined value. Because the red color of blood can interfere with the accuracy of the measurement, measurements are taken at two wavelengths in order to permit a first order subtraction of the background color of the blood. Furthermore, two wavelength readings permit a second order correction to eliminate chromatography effects resulting from variations in the hematocrit levels among various blood samples. Such devices are inconvenient to use and may be prone to inaccurate results if the cover becomes inoperative or if the user elects not to take the time to perform the pre-wetting calibration step.

U.S. Pat. No. 6,979,571 describes another test strip reader wherein a protective shroud is used to separate the test strip from the optics of the device. The shroud is provided with a hood, camming members and fingers for guiding the test strip into a groove formed in the shroud to align the test strip with the device optics. Such devices are expensive to manufacture, inconvenient to use, and vulnerable to mechanical failure due to the precision location necessary for the fingers and camming members.

DETAILED DESCRIPTION OF THE ILLUSTRATIVE EMBODIMENTS

For the purposes of promoting an understanding of the principles of the invention, reference will now be made to a number of illustrative embodiments shown in the attached drawings and specific language will be used to describe the same.

Figures 1A, 1B:
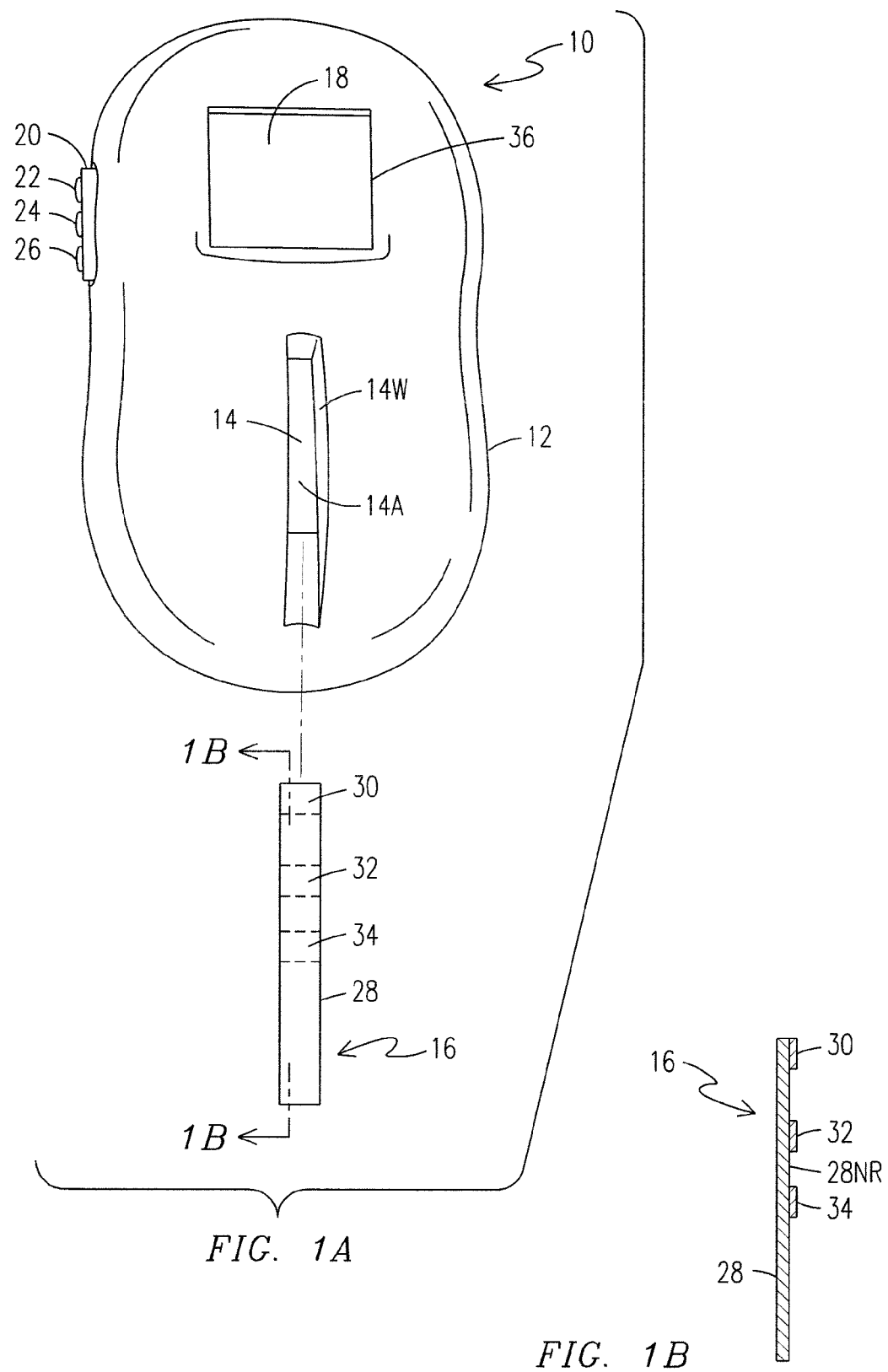
FIG. 1A is a top plan view of an electronic device for analyzing aqueous solutions to which a test element has been exposed.
FIG. 1B is a cross-sectional view of the test element of FIG. 1A as viewed along section lines 1B-1B.

Referring now to FIG. 1A, a top plan view of an electronic device 10 is shown for analyzing aqueous solutions. In the illustrated embodiment, the electronic device 10 includes a housing 12 defining a test element receiving port 14 configured to receive a test element 16 that has been exposed to an aqueous solution. The housing 12 defines an opening 36 that is sized to expose an electronic display unit 18 that forms part of the electrical circuitry carried by the housing 12. A switch pad or switch member 20 is positioned on one side of the housing 12, and a number of switches 22, 24 and 26 extend from the housing 12 through the switch pad or member 20. The housing 12 may be formed from a conventional molded plastic material, although other materials and/or material compositions are contemplated.

Referring now to FIG. 1B, a cross-sectional view of the test element 16 of FIG. 1A, as viewed along section lines 1B-1B, is shown. The test element 16 is formed of a flexible substrate 28 having a number of pads attached thereto. In the illustrated embodiment, three such pads 30, 32 and 34 are attached to one side of the flexible substrate 28, although more or fewer such pads may alternatively be attached to the substrate 28. Each of the pads 30, 32 and 34 is chemically treated in a conventional manner and with respective chemical reagent such that each of the pads 30, 32 and 34 react with an aqueous solution when exposed thereto and change to a color that is indicative of a corresponding characteristic of the aqueous solution. In the illustrated embodiment, for example, the test element 16 is a test strip that may be used to test the chlorine or bromine concentration, the pH level and total alkalinity of pool or spa water. In this example, one of the chemically treated pads, e.g., pad 30, is chemically treated such that it will change color, when exposed to an aqueous solution that is indicative of chlorine or bromine concentration of the aqueous solution. The pads 32 and 34 are likewise chemically treated such that one of the pads, e.g., pad 32 will change, when exposed to an aqueous solution, to a color that is indicative of a pH level of the aqueous solution, and the other pad, e.g., pad 34, will change, when exposed to the aqueous solution, to a color that is indicative of the total alkalinity of the aqueous solution.

To analyze the pool or spa water, the test element 16 is typically exposed to the pool or spa water, and a chemical reaction then takes place between the chemicals on each of the pads 30, 32 and 34 and the pool or spa water. This causes each of the pads to change to a color that is indicative of the corresponding pool or spa water characteristic, as just described. The colors of the pads 30, 32 and 34 are then typically compared visually to a color chart that maps pad color to a corresponding pool or spa water characteristic. The color chart may, for example, be imprinted on, or attached to, a container or vessel in which the test elements are supplied. Typically ideal ranges for pools and spas are 1-3 ppm of chlorine (or 3-6 ppm of bromine), 80-120 ppm total alkalinity, and 7.2-7.6 pH, and in this exemplary embodiment the pads 30, 32 and 34 are chemically treated in a conventional manner and with conventional chemical compositions to provide for detection of chlorine or bromine, total alkalinity and pH in these ranges. It will be appreciated, however, that the pads may alternatively or additionally be chemically treated to provide for detection of such characteristics in other ranges. The pads themselves may be formed of any bibulous material, and one example of such a bibulous material that may be used to form the pads 30, 32 and 34 is, but should not be limited to, filter paper.

The test elements 16 just described are conventionally provided with a substrate 28 that is white in color to provide a neutral background for visually comparing the colors of the pads 30, 32 and 34 to a color chart as just described. In the embodiment illustrated in FIGS. 1A and 1B, the test element 16 differs from such conventional test elements in that the substrate 28 is configured to control (minimize, or at least reduce) radiation reflection and transmittance during interrogation of the test pads 30, 32, 34 to facilitate analysis of the test element 16 by the electronic device 10. The substrate 28 may be opaque. The term opaque is used herein to include material that is effectively opaque even though it may allow the transmittance of a small amount of radiation of interest; i.e. its transmittance of radiation in the wavelengths detected by the device 10 is sufficiently low so as not to change the output reading of the device for a given test sample between readings made in darkness and readings made in outdoor sunlight conditions. The substrate 28 may be formed of a material that is sufficiently thick to be opaque, or a non-opaque material may be coated on one or both sides with an opaque coating. At least one surface 28NR of the substrate may be a non-reflective surface, either having a sufficiently dark color and/or being made of an anti-reflective material and/or having an anti-reflective coating applied to the surface 28NR. The term non-reflective as used herein means reflecting an amount of incident radiation that is no more than 10% of the amount of incident radiation that is reflected from a white (fully reflective) background in the wavelengths of interest (typically the full visible light spectrum). In one embodiment, the substrate 28 is black polystyrene.

For purposes of this disclosure, the electronic device 10 will be described herein as being configured to determine the colors of the pads 30, 32 and 34 of the test element 16 illustrated in FIGS. 1A and 1B, and to determine and display on the display unit 18 numerical values of the corresponding chlorine (or bromine), alkalinity and pH levels of an aqueous solution to which the test element 16 has been exposed. It will be understood, however, that the test element 16 may alternatively have more or fewer such pads attached thereto, and/or be chemically treated with alternative chemical compositions configured to change color as a function of one or more different characteristics the aqueous solution. Examples of such alternative characteristics of the aqueous solution to which at least one pad arranged on the substrate 28 may be sensitive to include, but are not limited to, ammonia concentration, nitrite concentration, nitrate concentration, solution hardness, peracetic acid concentration, and chloramine concentration.

Figure 2:
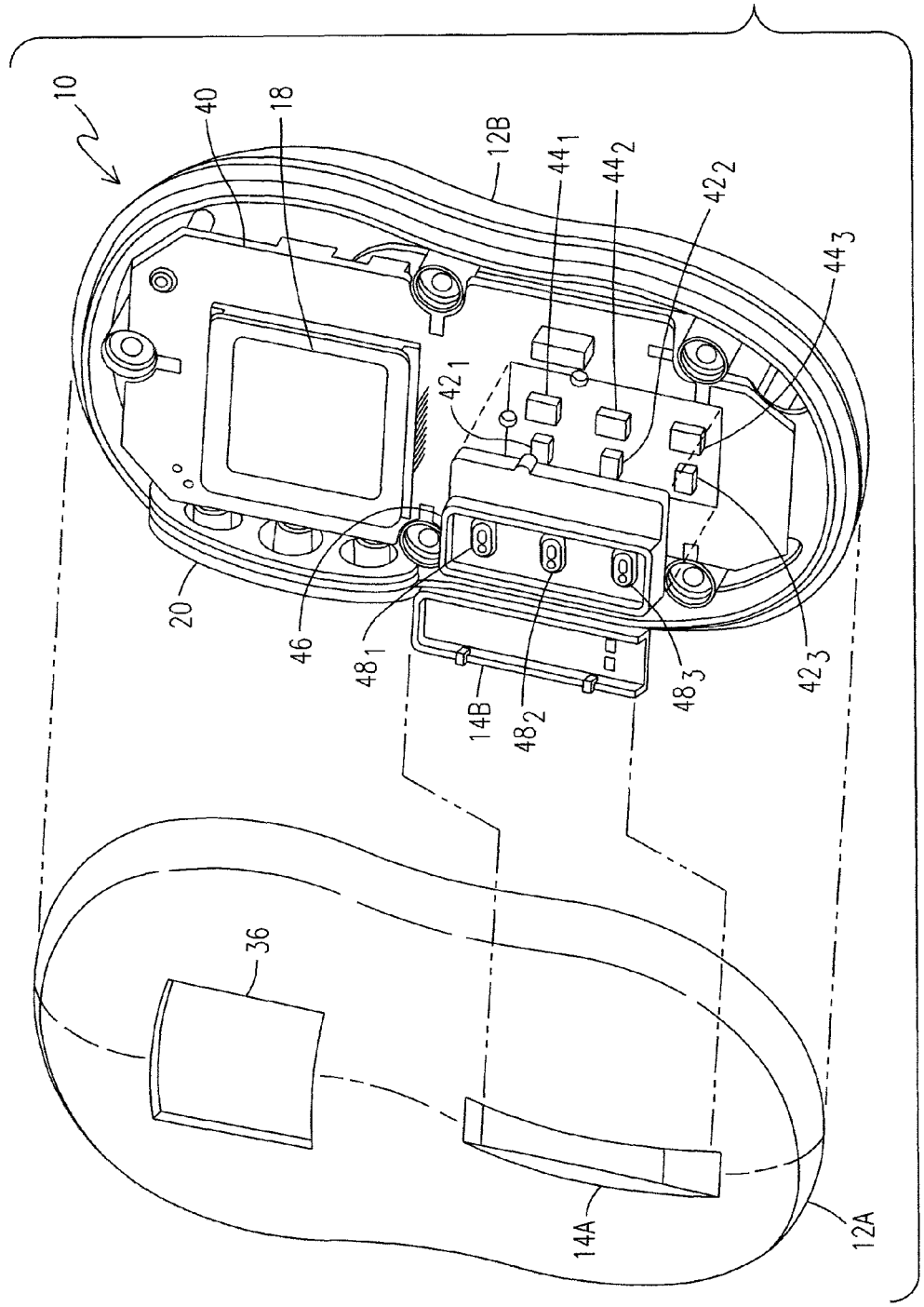
FIG. 2 is a partial assembly view of the device shown in FIG. 1A for analyzing aqueous solutions.

Referring now to FIG. 2, a partial assembly view of the electronic device 10 for analyzing aqueous solutions is shown. In the illustrated embodiment, the housing 12 is shown as having a top portion or cover 12A and a bottom portion 12B. The top portion or cover 12A defines the opening 36 through which the display unit 18 is visible and further defines a slot 14A that defines, in part, the test element receiving port 14 of FIG. 1A. A test element placement member 14B is configured to be attached to the underside of the top portion or cover 12A of the housing 12, and juxtaposed with the slot 14A such that a test element 16 received in the slot 14A is received on the test element placement member 14B with the bibulous material of the pads 30, 32, 34 positioned against the test element placement member 14B. Together, the slot 14A and the test element placement member 14B define the test element receiving port 14.

The bottom portion 12B of the housing 12 is sized to receive therein a circuit board 40 having the electronic display unit 18, as well as a number of additional electrical components, mounted thereto. The additional electrical components include, for example, a number of conventional radiation detection circuits and a corresponding number of conventional radiation sources. Generally, the number of radiation sources and radiation detection circuits will correspond to the number of pads arranged on the test element 16. In the embodiment illustrated in the attached drawings, for example, the test element 16 has three such pads 30, 32 and 34 mounted thereto, and the circuit board 40 in this embodiment accordingly has three radiation sources $42_1$-$42_3$ mounted thereto and three corresponding radiation detection circuits $44_1$-$44_3$ also mounted thereto. A radiation guide structure 46 defines three corresponding radiation guides members $48_1$-$48_3$, wherein the radiation guide structure 46 is configured to be received on the circuit board 40 such that each radiation guide member $48_1$-$48_3$ is aligned with a corresponding pair of the radiation sources $42_1$-$42_3$ and radiation detection circuits $44_1$-$44_3$, and such that the top surfaces of all of the radiation guide members $48_1$-$48_3$ are juxtaposed with a bottom surface of the test element placement member 14B when the top portion or cover 12A engages the bottom portion 12B.

Figure 3:
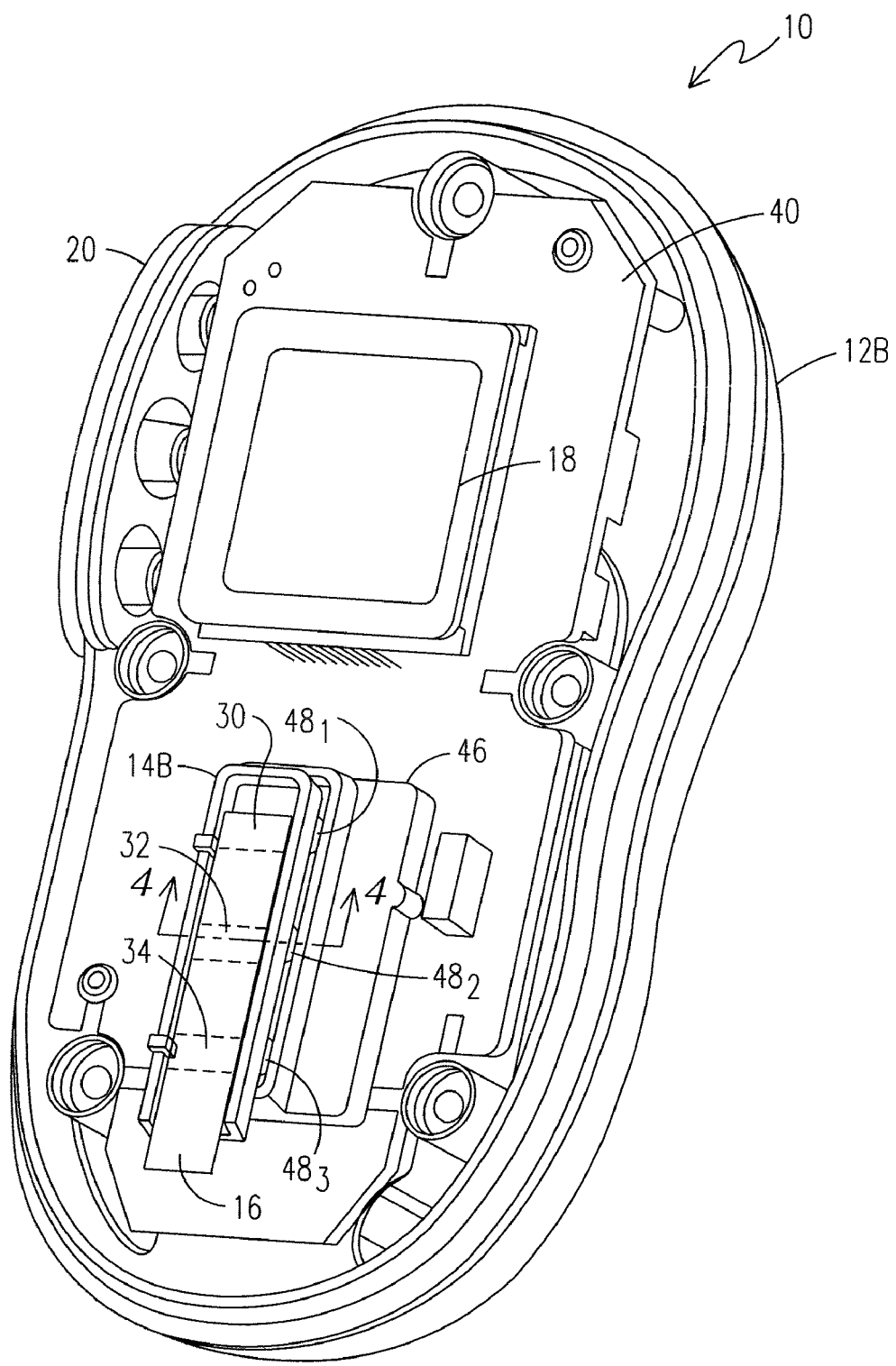
FIG. 3 is an assembled view of a portion of the device shown FIG. 2 further illustrated with a test element operatively received by the device.

Referring now to FIG. 3, an assembled view of the bottom portion 12B of the housing 12 is shown with the circuit board 40 mounted thereto and with the radiation guide structure 46 positioned over the radiation sources $42_1$-$42_3$ and radiation detection circuits $44_1$-$44_3$. The test element placement member 14B is shown in FIG. 3 as being juxtaposed over the radiation guide structure 46 as it would be when the top portion or cover 12A of the housing 12 is mounted to the bottom portion 12B. A test element 16 is superimposed onto FIG. 3 to illustrate that when the test element 16 is received on the test element placement member 14B with the illustrated and predefined orientation, the pads 30, 32 and 34 arranged on the test element 16 are juxtaposed over corresponding ones of the radiation guide members $48_1$-$48_3$. Radiation emitted by the radiation sources $42_1$-$42_3$ is guided by corresponding ones of the radiation guide members $48_1$-$48_3$ to direct the emitted radiation to corresponding ones of the pads 30, 32 and 34 of the test element 16, and to also direct the resulting radiation reflected by each of the pads 30, 32 and 34 to corresponding ones of the radiation detection circuits $44_1$-$44_3$. Signals produced by the radiation detection circuits $44_1$-$44_3$ in response to the reflected radiation are then used to determine the different colors of the pads 30, 32 and 34 that result from exposure of the test element 16 to an aqueous solution, as will b described in greater detail hereinafter.

Figure 4:
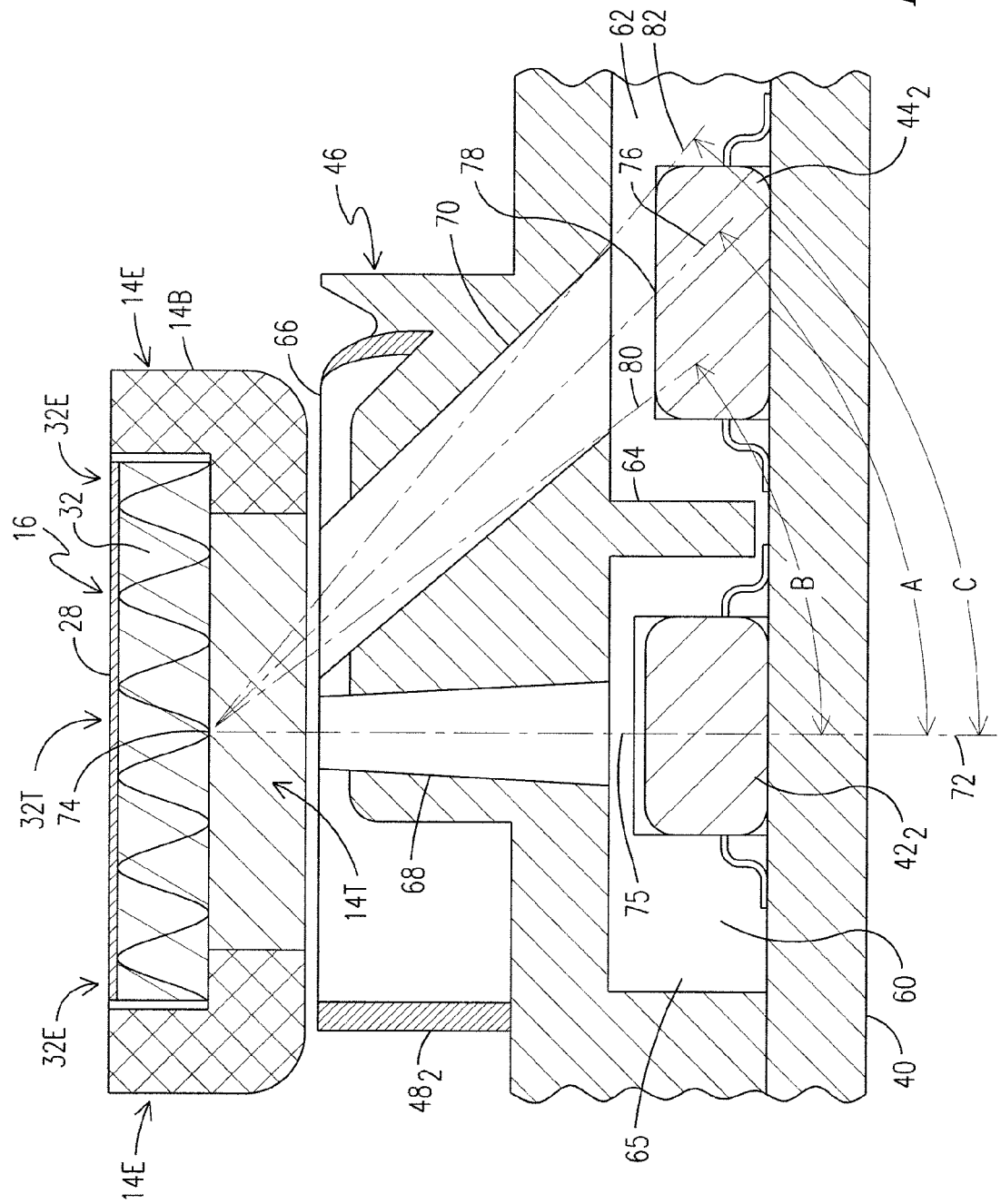
FIG. 4 is a cross-sectional view of a portion of the device of FIG. 3 viewed along section lines 4-4.

Referring now to FIG. 4, a cross-section of the radiation guide structure 46, the test element placement member 14B and the test element 16 is shown as viewed along section lines 4-4 of FIG. 3. In the illustrated embodiment, the radiation source $42_2$ and the radiation detection circuit $44_2$ are shown as being mounted to the circuit board 40. The radiation guide member $48_2$ defines a first cavity 60 and a second cavity 62 with a wall 64 defined between the two cavities 60 and 62. The cavities 60 and 62 are sized to receive the radiation source $42_2$ and the radiation detection circuit $44_2$ respectively therein when the radiation guide structure 46 is positioned on the circuit board 40 as illustrated in FIGS. 2 and 3. The wall 64 separates the cavities 60 and 62 to minimize radiation transmission therebetween. An outer wall 65 surrounds and encloses the cavities 60 and 62 to define the radiation guide member $48_2$.

The radiation guide member $48_2$ defines a radiation guide in the form of a passageway 68 that extends between the cavity 60 and a top portion 66 of the radiation guide member $48_2$. The passageway 68 is an open passageway having one end open to the cavity 60 and an opposite end defining an opening in the top portion 66 of the radiation guide member $48_2$. The radiation guide member $48_2$ defines another radiation guide 70 therethrough in the form of another passageway extending between the top portion 66 of the radiation guide member $48_2$ and the cavity 62. The passageway 70 is an open passageway having one end open to the cavity 62 and an opposite end defining an opening in the top portion 66 of the radiation guide member $48_2$. In the illustrated embodiment, the radiation guides 68 and 70 are circular in cross-section, although other cross-sectional shapes of the radiation guides 68 and 70 are contemplated.

The radiation guide 68 defines a longitudinal axis 72 extending centrally therethrough. In the illustrated embodiment, the longitudinal axis 72 defined by the radiation guide 68 extends through approximately a central portion of the radiation source $42_2$ and also through approximately a central portion of the test element placement member 14B at a location corresponding to a center point 74 of the pad 32 of a test element 16 when the test element 16 is received on the test element placement member 14B with the predefined orientation relative to the test element placement member 14B. The radiation guide 70 similarly defines a longitudinal axis 76 extending centrally therethrough. In the illustrated embodiment, the longitudinal axis 76 defined by the radiation guide 70 extends through approximately a central portion of the radiation detection circuit $44_2$ and also through the test element placement member 14B at a location such that the longitudinal axis 76 bisects the axis 72 at approximately the center point 74 of the pad 32 of the test element 16. It will be appreciated that the radiation guides 68 and 70 may be alternatively positioned relative to the test element placement member 14B, or vice versa, such that the bisection point of the longitudinal axes 72 and 76 is positioned at any desired location of the pad 32. Likewise, either or both of the radiation guides 68 and 70 may be alternatively positioned relative to the cavities 60 and 62 respectively such that the axis 72 extends non-centrally through the radiation source $42_2$ and/or that the axis 76 extends non-centrally through the radiation detection circuit $44_2$.

The side wall of the radiation guide 70 defines boundary axes 80 and 82 extending from the bisection point of the axes 72 and 76 to opposing locations of the side wall at the opening of the radiation guide 70 adjacent to the cavity 62, as illustrated in FIG. 4. The longitudinal axes 72 and 76 define an angle, A, therebetween, the longitudinal axis 72 and the boundary axis 80 of the radiation guide 70 define another angle, B, therebetween, and the longitudinal axis 72 and the other boundary axis 82 of the radiation guide 70 define yet another angle, C, therebetween. The angles A, B and C are typically selected such that the longitudinal axis 72 defined through the radiation guide 68 extends through a substantially central point 75 defined on the top surface of the radiation source $42_2$, the longitudinal axis 76 defined through the radiation guide 70 extends through a substantially central point 78 defined on the top surface of the radiation detection circuit $44_2$, and the boundary axes 80 and 82, extend through a top portion of the radiation detection circuit $44_2$ adjacent to the sides of the radiation detection circuit $44_2$. With this arrangement, radiation emitted by the radiation source $42_2$ extends through the radiation guide 68 to the pad 32 of the test element 16, and is reflected from the pad 32 of the test element 16 through the radiation guide 70 and onto the top surface of the radiation detection circuit $44_2$. In one exemplary embodiment, the angle, A, is approximately 45°, the angle, B, is approximately 37.73°, and the angle, C, is approximately 50.804°, although other angles of A, B and C are contemplated.

Radiation emitted by the radiation source $42_2$ passes through the radiation guide 68, through the test element placement member 14B and strikes the surface of the pad 32 that is arranged on the substrate 28 of the test element 16. Radiation is then reflected from the surface of the pad 32 and extends through the radiation guide 70 through the top surface 78 of the radiation detection circuit $44_2$. The test element placement member 14B is accordingly formed of a material that is radiation transmissive, particularly in the frequency range of the radiation source $44_2$, and that is chemically inert to the aqueous solution and the test pad chemical compositions. The radiation guide member $48_2$ is conversely formed of a material that does not transmit radiation therethrough so that the radiation may be confined by the radiation guides 68 and 70. In one illustrative embodiment, the radiation guide structure 46 is formed of pigmented nylon and the test element placement member 14B is formed of polycarbonate resin such as sold under the registered trademark LEXAN® although other materials and/or material compositions are contemplated for either structure.

It will be understood that while operation of the radiation guide structure 46 was described hereinabove with respect to the radiation guide member $48_2$, any additional radiation guide members defined by the radiation guide structure 46, e.g., radiation guide members $48_1$ and $48_3$, operate identically with respect to corresponding pairs of radiation sources and radiation detection circuits.

Figure 5:
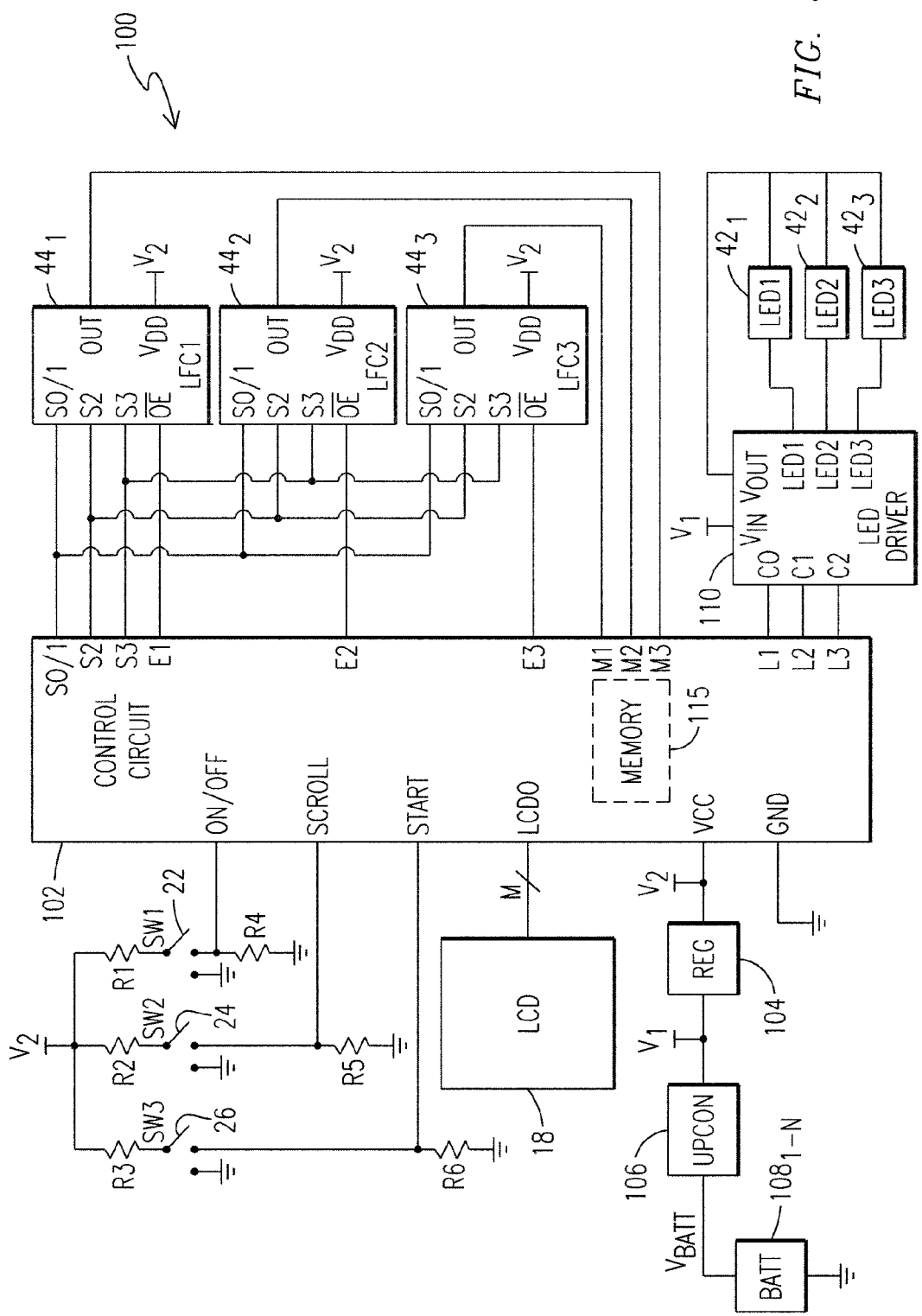
FIG. 5 is a schematic diagram illustrating some of the electrical circuitry mounted to the circuit board of FIGS. 2 and 3.

Referring now to FIG. 5, a schematic diagram is shown of one illustrative embodiment of some of the electrical circuitry 100 mounted to the circuit board 40 illustrated in FIGS. 2 and 3. The electrical circuitry 100 generally manages the overall operation of the electronic device 10, including determining one or more characteristics of an aqueous solution to which a test element 16 has been exposed. In the illustrated embodiment, a control circuit 102 is configured to control operation of the electronic device 10. The control circuit 102 has, or has access to, a memory unit 115. The memory unit 115 has stored therein one or more software processes that are executable by the control circuit 102 to determine one or more characteristics of an aqueous solution to which the test element 16 has been exposed, as a function of measurement signals produced by one or more corresponding radiation detection circuits. In the illustrated embodiment, three such radiation detection circuits $44_1$-$44_3$ are shown, and in this embodiment the electronic device 10 is configured to determine three characteristics of an aqueous solution to which the test element 16 has been exposed. It will be understood, however, that the electronic device 10 may include more or fewer such radiation detection circuits and the control circuit 102 may be configured as described herein to control any such number of radiation detection circuits to determine any corresponding number of characteristics of an aqueous solution to which the test element 16 has been exposed.

The control circuit 102 includes a VCC input receiving a regulated voltage, V2, produced at an output of a conventional voltage regulator circuit 104, and a GND terminal that is connected to a reference potential, e.g., ground potential. The voltage regulator circuit 104 has an input receiving a voltage, V1, produced at an output of a conventional voltage up-converter circuit 106. The voltage up-converter circuit 106 has an input receiving a battery voltage, $V_{BATT}$ produced by any number, N, of conventional batteries $108_1$-$108_N$, wherein N may be any positive integer. Illustratively, the number N of batteries may be provided in the form of one or more conventional dry-cell batteries that may or may not rechargeable in a conventional manner. In one exemplary embodiment, for example, the circuit 100 may include two or more conventional dry-cell batteries connected to produce a battery voltage, $V_{BATT}$, of about 3.0 volts. In this embodiment, the voltage up-converter circuit 106 may be, for example, a conventional step-up DC-DC converter configured to step-up the battery voltage, $V_{BATT}$, of approximately 3.0 volts to an output voltage, V1, of approximately 5.0 volts. In one specific embodiment, for example, the voltage up-converter circuit may be a MAX1674EUA step-up DC-DC converter circuit produced by Maxim Integrated Products. The voltage regulator circuit 104, in this exemplary embodiment, may be, for example, a SP6201EM5-L-3.3/TR voltage regulator produced by Sipex Corporation. In this exemplary embodiment, the battery voltage, $V_{BATT}$, is approximately 3.0 volts nominal, the up-converter voltage V1, is approximately 5.0 volts, and the regulated voltage V2, is also about 5.0 volts, although it will be understood that the present disclosure contemplates other values of $V_{BATT}$, V1 and V2 and any conventional electronic circuitry necessary to produce such voltages.

The circuitry 100 further includes a conventional display device 18, as described hereinabove, having a number, M, of inputs that are electrically connected to a corresponding number, M, of outputs of the control circuit 102, where M may be any positive integer. In the illustrated embodiment, the display device 18 is provided in the form of a conventional liquid crystal display (LCD), one example of which is a conventional 67 segment, 3-MUX LCD unit having 24 data inputs and three control inputs. It will be understood, however, that the display device 18 may be provided in the form of other conventional LCD display units or alternatively in the form of one or more other conventional display units including, but not limited to, one or more LED display units, one or more vacuum-fluorescent display units, or the like.

The control circuit 102 further has an on/off input that is electrically connected to one terminal of the switch 22 and also to one end of a resister, R4, having an opposite end electrically connected to ground potential. Another terminal of the switch 22 is electrically connected to one end of a resister, R1, the opposite end of which is electrically connected to the potential V2. Yet another terminal of the switch is connected to ground potential. The control circuit 102 is response to the "on" state of the switch 22, e.g., when the ends of the resistors R1 and R4 are electrically connected together by the switch 22, to power up to an operational state and to activate at least some of the electrical components of the electrical circuitry 100. The control circuit is responsive to the "off" state of the switch 22, e.g., when the end of the resistor R4 is connected by the switch 22 to ground potential, to power down or enter a conventional low-power "sleep" mode, and to deactivate at least some of the electrical components of the electronic circuitry 100.

The control circuit 102 further includes a scroll input which is electrically connected to one terminal of the switch 24 and also to one end of a resister, R5, having an opposite end that is electrically connected to ground potential. Another terminal of the switch 24 is electrically connected to one end of a resister, R2, having an opposite end electrically connected to the potential V2. Yet another terminal of the switch 24 is electrically connected to ground potential. The control circuit 102 is responsive to a first activation of the "on" state of the scroll switch 24, e.g., when the two ends of the resistors R2 and R5 are electrically connected together by the switch 24, to display on the display unit 18 a previous set of aqueous solution characteristics that is stored in the memory unit 115, as will be described in greater detail hereinafter. The control circuit 102 is further responsive to successive activations of the "on" state of the scroll switch 24 within predefined time periods of each other to display on the display unit 18 previous sets of aqueous solution characteristics that have been stored in the memory unit 115, as will also be described hereinafter. The control circuit 102 is illustratively configured to take no action when the switch 24 is in the "off" state, e.g., when the resistor R2 is electrically connected by the switch 24 to ground potential.

The control circuit 102 further includes a START input that is electrically connected to one terminal of the switch 26 and also to one end of a resister, R6, having an opposite end that is electrically connected to ground potential. Another terminal of the switch 26 is electrically connected to one end of a resister, R3, having an opposite end that is electrically connected to the potential V2. Yet another terminal of the switch 26 is electrically connected to ground potential. The control circuit 102 is responsive to the "on" state of the switch 26, e.g., when the resistors R3 and R6 are electrically connected together by the switch 26, to begin processing a test element 16 that has been received on the test element placement member 14B to determine one or more characteristics of an aqueous solution to which the test element 16 has been exposed, as will be described in greater detail hereinafter. The control circuit 102 is illustratively configured to take no action when the switch 26 is in the "off" state, e.g., when the resistor R3 is electrically connected by the switch 26 to ground potential.

The electrical circuitry 100 further includes a number of radiation sources, as well as circuitry that is controllable by the control circuit 102 to activate and deactivate such radiation sources. In the embodiment illustrated in FIG. 5, the radiation sources are implemented in the form of three light emitting diodes (LEDs) that are each electrically connected to a conventional LED driver circuit 110 that is itself electrically connected to the control circuit 102. Illustratively, the LED driver circuit 110 may be provided in the form of a CAT3604-channel white LED driver manufactured by Catalyst Semi-Conductor, Inc., and each of the radiation emitting diodes $42_1$-$42_3$ are provided in the form of conventional LEDs configured to produce white light. It will be understood, however, that other radiation sources configured to produce radiation in any desired frequency range are contemplated, as well as any supporting circuitry that may be necessary to drive any such alternative radiation sources.

In the embodiment illustrated in FIG. 5, LED outputs, L1-L3, of the control circuit 102 are each electrically connected to corresponding control inputs, C0-C2, of the LED driver circuit 110. A supply voltage input, $V_{IN}$, of the LED driver circuit 110 receives the voltage V1 produced by the up-converter circuit 106. The LED driver circuit 110 includes a charge pump that boosts the voltage V1 to an output voltage, $V_{out}$, suitable for achieving a nominal LED current. The output, $V_{OUT}$, of the LED driver circuit 110 is electrically connected to the anodes of each of the LEDs, $42_1$-$42_3$, and the cathodes of each of the LEDs, $42_1$-$42_3$, are electrically connected to corresponding LED inputs, LED1-LED3, of the LED driver circuit 110. In this embodiment, the LED driver circuit 110 includes a number of dedicated current sink regulators each connected to a corresponding one of the LED inputs, LED1-LED3, and each of which are controllable according to the activation state of the control inputs C0-C2, to thereby control activation and deactivation of the LEDs, $42_1$-$42_3$. In the illustrated embodiment, for example, all of the LEDs, $42_1$-$42_3$, are in the off (non-illuminating) states when each of the control inputs, C0-C2, are controlled to a logic high state. The first LED, $42_1$, may be activated (illuminated) by controlling either or both of the inputs C0 and C1 to a logic low state and the input C2 to a logic high state or by controlling both of the inputs C0 and C1 to logic low states and the input C2 to a logic low state, the second LED, $42_2$, can be activated (illuminated) by controlling either or both of the inputs C0 and C1 to a logic low state and the input C2 to a logic high state or by controlling the input C0 to a high logic high state, controlling the input C1 to a logic low state and controlling the input C2 to a logic low state, and the third LED, $42_3$, can be activated (illuminated) by controlling either, but not both, of the inputs C0 and C1 to a logic low state and the input C2 to a logic high state or by controlling the input C0 to a logic low state, the input C1 to a logic high state and controlling the input C2 to a logic low state.

It will be appreciated that other conventional LED driver circuits can be used to control operation of the LEDs, $42_1$-$42_3$, via the control circuit 102. It will further be appreciated that one or more of the radiation sources $42_1$-$42_3$ may be configured to emit radiation in other visible frequency ranges and/or in non-visible frequency ranges. The driver circuit 110 will, in any such case, be provided in the form of one or more conventional driver circuits configured to control activation and deactivation of the one or more radiation sources based on any number of control signals provided thereto by the control circuit 102.

The electronic circuitry 100 further includes a number of radiation detection circuits as described hereinabove with respect to FIGS. 1A and 2-4. In the embodiment illustrated in FIG. 5, three such radiation detection circuits, $44_1$-$44_3$, are provided in the form of conventional radiation detection circuits each configured to produce a number of measurement signals corresponding to radiation reflected thereon from one of the chemically treated pads 30, 32 or 34 of the test element 16 as a result of being irradiated by a corresponding one of the radiation sources. In one specific embodiment wherein the one or more radiation sources are provided in the form of LEDs configured to irradiate visible light, e.g., white light, the radiation detection circuits $44_1$-$44_3$ are each provided in the form of a TCS230D TR color light-to-frequency converter circuit manufactured by Texas Advanced Optical Electronic Solutions, Inc. In this embodiment, select outputs S0/1, S2 and S3 of the control circuit 102 are each electrically connected to corresponding select inputs, S0/1, S2 and S3 of each of the radiation-to-frequency converter circuits $44_1$-$44_3$, where S0/1 denotes two inputs S0 and S1 that are connected together externally to the circuits $44_1$-$44_3$. Additionally, three enable outputs, E1-E3, of the control circuit 102 are connected to output enable inputs, OE, of a different one of each of the light-to-frequency converter circuits $44_1$-$44_3$. Outputs, OUT, of each of the light-to-frequency converter circuits, $44_1$-$44_3$, are electrically connected to corresponding measurement signal inputs, M1-M3, of the control circuit 102. Each of the light-to-frequency converter circuits, $44_1$-$44_3$, includes an array of photodiodes arranged on the top surface thereof, and a current-to-frequency converter configured to produce an output signal in the form of a square wave signal having a frequency that is directly proportional to the intensity of radiation detected by the array of photodiodes. Illustratively, the array of photodiodes includes 16 photodiodes having blue filters, 16 photodiodes having green filters, 16 photodiodes having red filters, and 16 photodiodes having no filters, e.g., that are clear. All photodiodes of the same color are electrically connected in parallel, and can be separately activated as a function of logic states of the selection inputs S2 and S3. For example, with S2 and S3 both in a logic low state, the red photo diodes are active, with S2 in the low logic state and S3 in the high logic state, the blue photo diodes are active, with S2 in the high logic state and S3 in the low logic state, the clear (no filter) photo diodes are active, and with S2 and S3 both in the logic high state, the green photo diodes are active.

The light-to-frequency converter circuits, $44_1$-$44_3$, are in a powered down state when the S0/1 inputs are both in a logic low state, and are configured to provide full-scale (100%) output frequency when the S0/1 inputs are both in a logic high state. The light-to-frequency converter circuits, $44_1$-$44_3$, may be individually selected for operation by controlling the logic state of each of the output enable inputs thereof. The control circuit 102 is configured to control each of the light-to-frequency converter circuits, $44_1$-$44_3$, to capture red, green, blue and white light frequency measurement signals during illumination of a corresponding chemically-treated pad 30, 32 or 34 of the test element 16. The control circuit 102 is further configured to pulse-accumulate or integrate each of the red, green, blue and white frequency signals to produce corresponding R, G, B and W signals each corresponding to the exposure, or the amount of light captured, over a given time period. The control circuit 102 is then configured as will be described in greater detail hereinafter, to process the R, G, B and W signals produced by each of the light-to-frequency converter circuits $44_1$-$44_3$ according to a different model to determine a corresponding characteristic of the aqueous solution to which the test element 16 was exposed.

It will be appreciated that the number of radiation detection circuits, $44_1$-$44_3$, may alternatively be configured to detect radiation in other visible and/or non-visible frequency ranges, in a manner consistent with alternate embodiments of the radiation sources, $42_1$-$42_3$, described hereinabove. It will further be appreciated that one or more of the radiation detection circuits, $44_1$-$44_3$, may be provided in the form of a conventional radiation-to-frequency converter, a radiation-to-voltage converter, a radiation-to-count converter, or the like.

It will further be appreciated that the electrical circuitry 100 illustrated in FIG. 5 represents major functional portions of a more detailed electrical circuit that will typically be mounted to the circuit board 40 of FIGS. 2 and 3. One example of such a more detailed electrical circuit is illustrated in U.S. Provisional Patent Application No. 60/836,322 which has been incorporated herein by reference.

Figure 6:
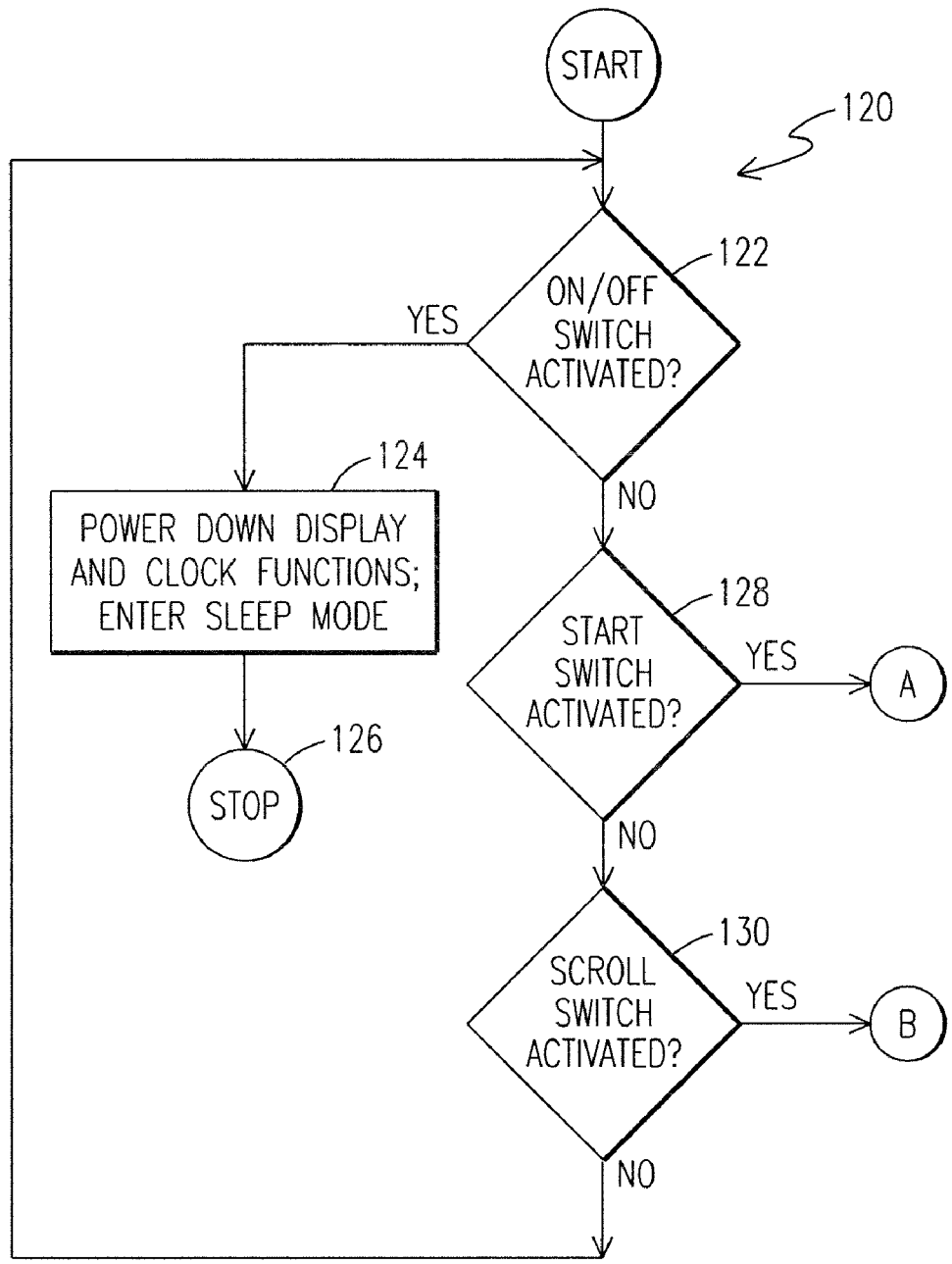
FIG. 6 is a flowchart of one illustrative embodiment of a process for controlling operation of the electronic device of FIGS. 1A and 2-5.

Referring now to FIG. 6, a flow chart is shown of one illustrative embodiment of a process 120 for controlling operation of the electronic device 10 of FIGS. 1A and 2-5. In the illustrated embodiment, the process 120 is stored in the memory unit 115 of the control circuit 102 in the form of instructions that are executable by the control circuit 102 to control operation of the device 10. It will be understood that one or more additional processes may be stored in the memory unit 115 and may be executable by the control circuit 102 to monitor, calibrate, test, and/or control other features and/or operation of the electronic device 10, including, for example, but not limited to, a low battery voltage monitoring function, one or more device calibrations, or the like. In any case, the process 120 will be described herein as being executed by the control circuit 102 pursuant to instructions stored in the memory unit 115.

In the illustrated embodiment, the process 120 begins after the electronic device 10 has concluded a power-up operation resulting from activation of the on/off switch 22 when the electronic device 10 was previously in its off state. The process 120 begins at step 122 where the control circuit 102 is operable to monitor the status of the on/off button 22 to determine whether the on/off button 22 has been activated. If so, the switch 22 has been activated to power down the electronic device 10, and the process execution accordingly advances to step 124 where the control circuit 102 is operable to power down a display unit 18 to deactivate all clock functions and to enter a power-safe "sleep" mode in a conventional manner. Thereafter at step 126, the process 120 stops until the device 10 is powered up again via activation of the on/off switch 22.

If, at step 122, the control circuit 102 determines that the on/off switch has not been activated (following power up of the device 10), process execution advances to step 128 where the control circuit 102 is operable to determine whether the START switch 124 has been activated. If so, process execution advances to subroutine A. If not, process execution advances to step 130 where the control circuit 102 is operable to determine wither the SCROLL switch 24 has been activated. If so, process execution advances to subroutine B, and otherwise process execution loops back to step 122.

Figure 7:
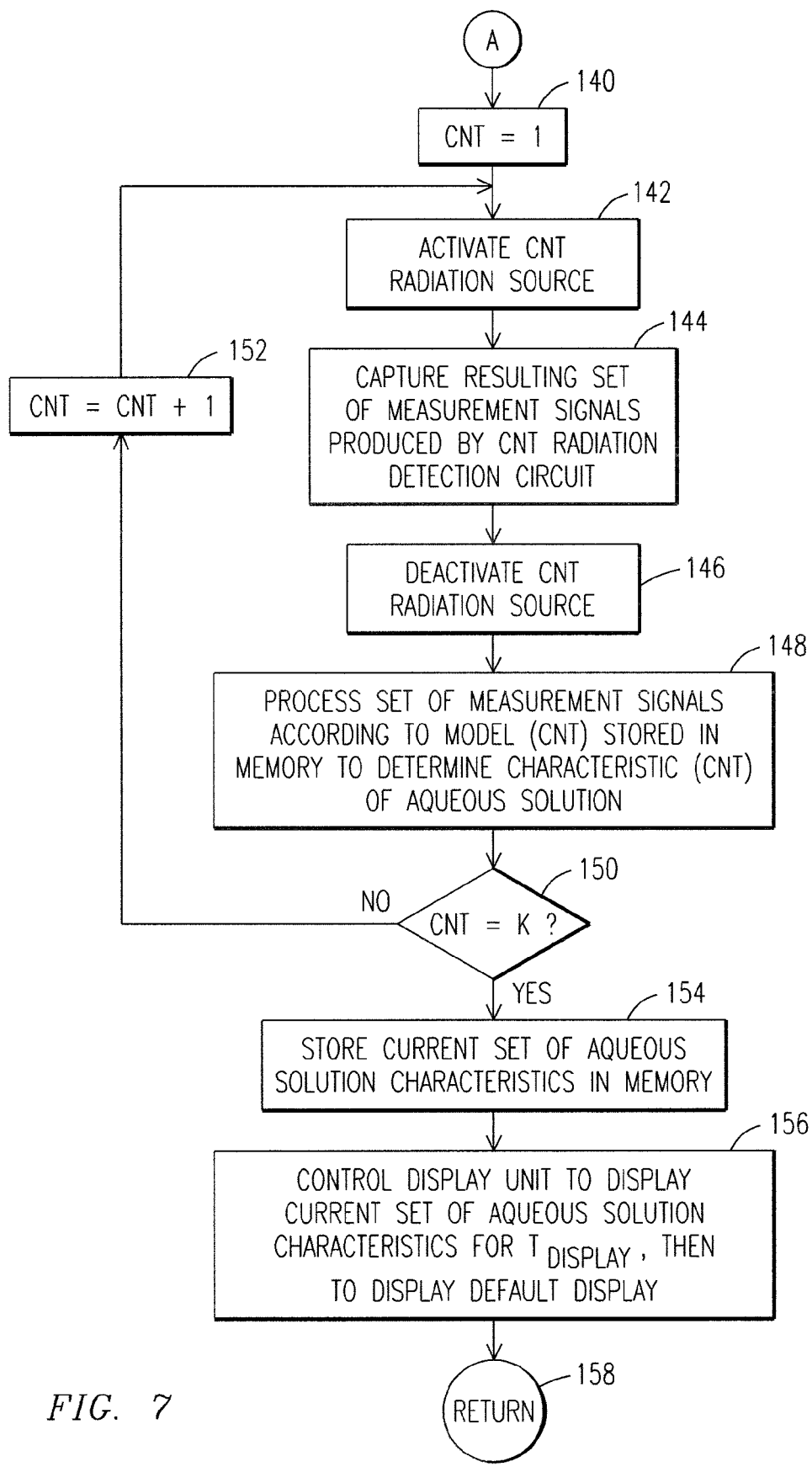
FIG. 7 is a flowchart of one illustrative embodiment of a subroutine that may be called by the process of FIG. 6, for processing information relating to the test element.

Referring now to FIG. 7, a flowchart of one illustrative embodiment of the subroutine A that was called from the "YES" branch of step 128 of the process 120 of FIG. 6, is shown. Subroutine A defines a process for processing a test element 16 received by the electronic device 10 to determine one or more characteristics of an aqueous solution to which the test element 16 has been exposed. Subroutine A begins at step 140 where a count value, CNT, is set equal to one. Thereafter at step 142, the control circuit 102 is operable to activate the radiation source corresponding to CNT. It will be understood that embodiments of the electronic device 10 configured to determine multiple characteristics of an aqueous solution, corresponding radiation source and radiation detection circuit pairs can be activated in any desired sequence to correspondingly determine the multiple characteristics of the aqueous solution in any desired sequence. Accordingly, the numbering of the various radiation source and radiation detection circuit pairs may be random.

In any case, the subroutine A advances from step 142 to step 144 where the resulting set of measurement signals produced by the "CNT" radiation detection circuit in response to irradiation of an appropriate portion of the test element 16 by a corresponding radiation source, as described hereinabove, are captured by the control circuit 102. Thereafter at step 146, the "CNT" radiation source is deactivated by the control circuit 102 as described hereinabove with respect to FIG. 5. Following step 146, subroutine advances to step 148 where the control circuit 102 is operable to process the set of measurement signals just captured according to a "CNT" model that is stored in the memory unit 115 to determine a corresponding "CNT" characteristic of the aqueous solution to which the test element 16 was exposed. Thereafter at step 150, the count value, CNT, is compared to a predefined integer value, K, wherein K corresponds to the total number of characteristics of the aqueous solution to which the test element 16 was exposed that are to be determined by the electronic device 10 pursuant to activation of the START switch 26. In the specific embodiment used throughout this document, for example, K=3. If, at step 150, the count value, CNT, is not equal to K, execution of subroutine A advances to step 152 where the count value, CNT, is incremented by one, and the subroutine A then loops back to step 142.

In the specific example implementation of the electronic device 10 that has been described herein, the aqueous solution may correspond to pool or spa water, and the test element 16 may have three chemically-treated pads 30, 32 and 34 for determining chlorine (or bromine) concentration, total alkalinity, and pH of the pool or spa water, respectively. In this example implementation, CNT=1 may correspond to radiation source $42_1$, radiation detection circuit $44_1$, characteristic 1 may correspond to chlorine (or bromine) concentration, and model 1 may correspond to a chlorine (or bromine) model that is stored in the memory unit 115 and that is configured to map the R, G, B and W signals resulting from operation of the radiation source $42_1$ and the radiation detection circuit $44_1$ to a corresponding chlorine (or bromine) concentration value. CNT=2 and CNT=3 may likewise correspond to like structures and models for determining corresponding alkalinity and pH values.

The subroutine A advances from the "YES" branch of step 150 to step 154 where the control circuit 102 is operable to store the current set of aqueous solution characteristics in the memory unit 115. In the example implementation just described, the set of aqueous solution characteristics correspond to chlorine (or bromine), alkalinity and pH values of pool or spa water, although it will be understood that a set of one or more aqueous solution characteristics may correspond to one or more additional or alternative aqueous solution characteristics of the type described herein. Additionally, although not specifically illustrated in FIG. 7, the control circuit 102 may be further operable at step 154 to store date and/or time values along with the set of aqueous solution characteristics in the memory unit 115, corresponding to the calendar date and/or time of day at which the set of aqueous solution characteristics were determined.

From step 154, the subroutine A advances to step 156 where the control circuit 102 is operable to control the display unit 18 to display the current set of aqueous solution characteristics for a predetermined time period, $T_{DISPLAY}$, and to then display a default display. $T_{DISPLAY}$ may be any desired time period, and the default display may be any desired display including, for example, but not limited to, a conventional power-saving display, a conventional screen-saver display, a company logo display or the like. In any case, execution of the subroutine A advances from step 156 to step 158 where the subroutine A is returned to step 128 of the process 120 of FIG. 6.

Figure 8:
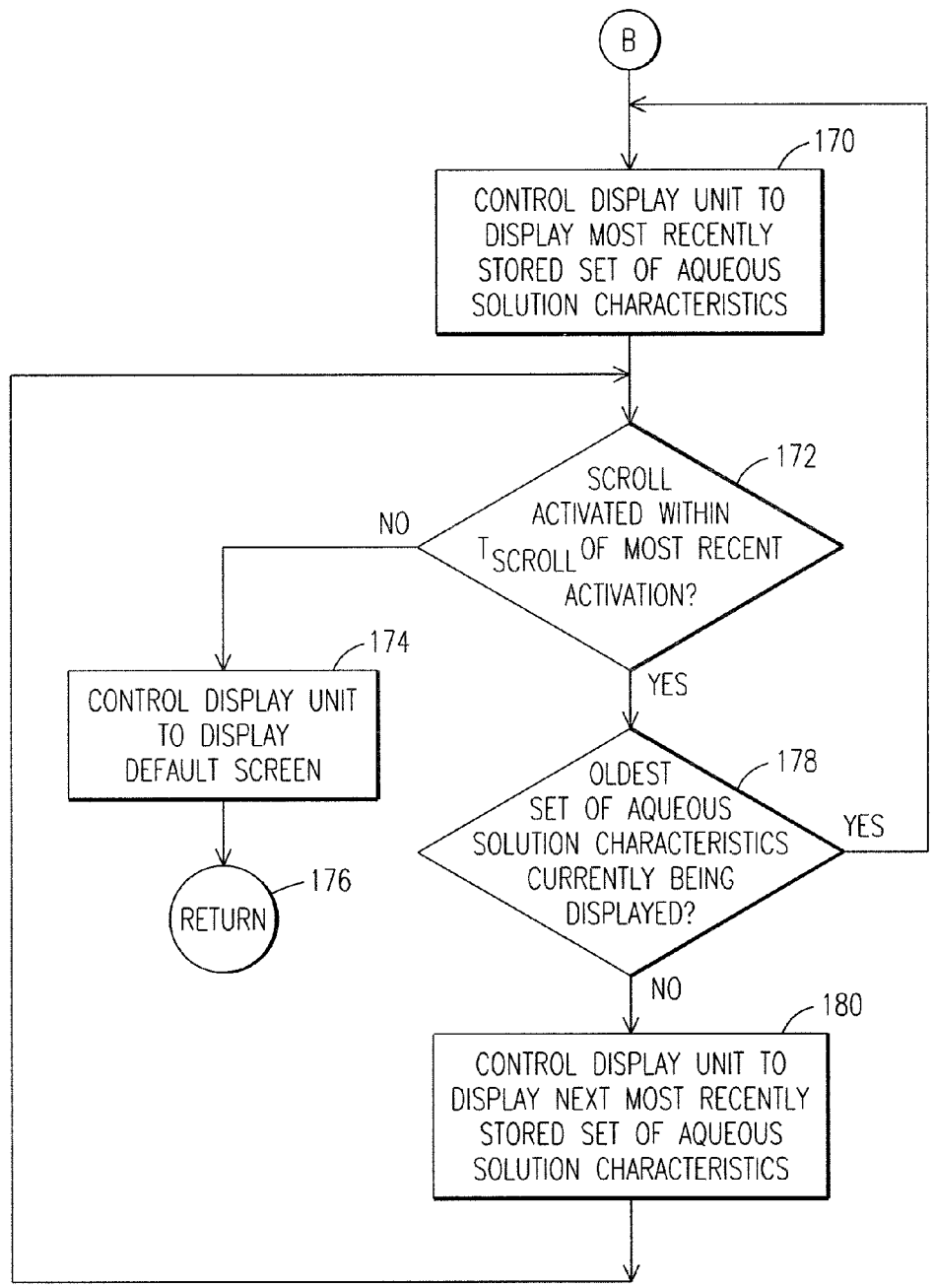
FIG. 8 is a flowchart of one illustrative embodiment of data scrolling subroutine that may be called by the process of FIG. 7.

Referring now to FIG. 8, a flowchart of one illustrative embodiment of the subroutine B that was called from the "YES" branch of step 130 of the process 120 of FIG. 6 is shown. The memory unit 115 of the control circuit 102 may be configured to store any number of sets of aqueous solution characteristics that may be scrolled through via successive activations of the scroll switch 24, and the control circuit 102 is operable to control such scrolling, in one embodiment, in accordance with the subroutine B of FIG. 8. The subroutine B begins at step 170 where the control circuit 102 is operable to control the display unit 18 to display the most recently stored set of aqueous solution characteristics. Thereafter at step 172, the control circuit 102 is operable to determine whether the scroll switch 24 has been activated within a time period, $T_{SCROLL}$, of the most recent activation of the scroll switch 26. The time period $T_{SCROLL}$ may be any desired time period, and if the control circuit 102 determines at step 172 that the scroll switch 24 has not been activated within $T_{SCROLL}$ of the most recent activation of the scroll switch 24, execution of the subroutine B advances to step 174 where the control circuit 102 is operable to control the display unit 18 to display the default screen as described hereinabove. Thereafter at step 176, execution of the subroutine B is returned to step 130 of the process 120 of FIG. 6.

If, at step 172, the control circuit 102 determines that the scroll switch 24 has been activated within $T_{SCROLL}$ of the most recent activation of the scroll switch 24, execution of the subroutine B advances to step 178 where the control circuit 102 is operable to determine whether the current set of aqueous solution characteristics being displayed on the display unit 18 corresponds to the oldest set of aqueous solution characteristics stored in the memory unit 115. If so, execution of the subroutine B loops back to step 170 to display the most recently stored set of aqueous solution characteristics. If, however, the control circuit 102 determines at step 178 that the set of aqueous solution characteristics currently being displayed is not the oldest set of aqueous solution characteristics stored in the memory unit 115, execution of the subroutine B advances to step 180 where the control circuit 102 is operable to control the display unit 18 to display the next most recently stored set of aqueous solution characteristics. From step 180, execution of the subroutine B loops back to step 172.

In one illustrative implementation of the electronic device 10, the memory unit 115 is configured to store L sets of aqueous solution characteristics, where L may be any positive integer. By successive activations of the scroll switch 24, each within the time period $T_{SCROLL}$ of the last activation of the scroll switch 24, the L sets of aqueous solution characteristics stored in the memory unit 115 are sequentially displayed beginning with the most recently stored set of aqueous solution characteristics and stepping sequentially to the oldest stored set of aqueous solution characteristics. When the last, or oldest, set of aqueous solution characteristics is displayed, the next activation of the scroll switch 24 will cause the most recently stored set of aqueous solution characteristics to be displayed. As new sets of aqueous solution characteristics are stored in the memory unit 115, the last, or oldest, sets of aqueous solution characteristics are overwritten so as to maintain only the most recent L sets aqueous solution characteristics stored in the memory unit 115. In one exemplary embodiment, L=9, although other values of L are contemplated. It will be appreciated that the memory unit 115 may alternatively be configured to store more or fewer sets of aqueous solution characteristics, and/or that the subroutine B may be modified to accomplish other scrolling strategies. Any such modifications to the subroutine B would be a mechanical step for a skilled programmer.

Referring again to FIG. 7, step 148 of the subroutine A comprises processing the set of measurement signals according to a particular model stored in the memory unit 115 to determine a corresponding characteristic of the aqueous solution to which a test element 16 has been exposed. Such a model may be provided in the form of one or more equations, graphs, tables or the like, and in one exemplary embodiment of the electronic device 10, three such models are provided with each such model comprising multiple equations.

Figure 9:
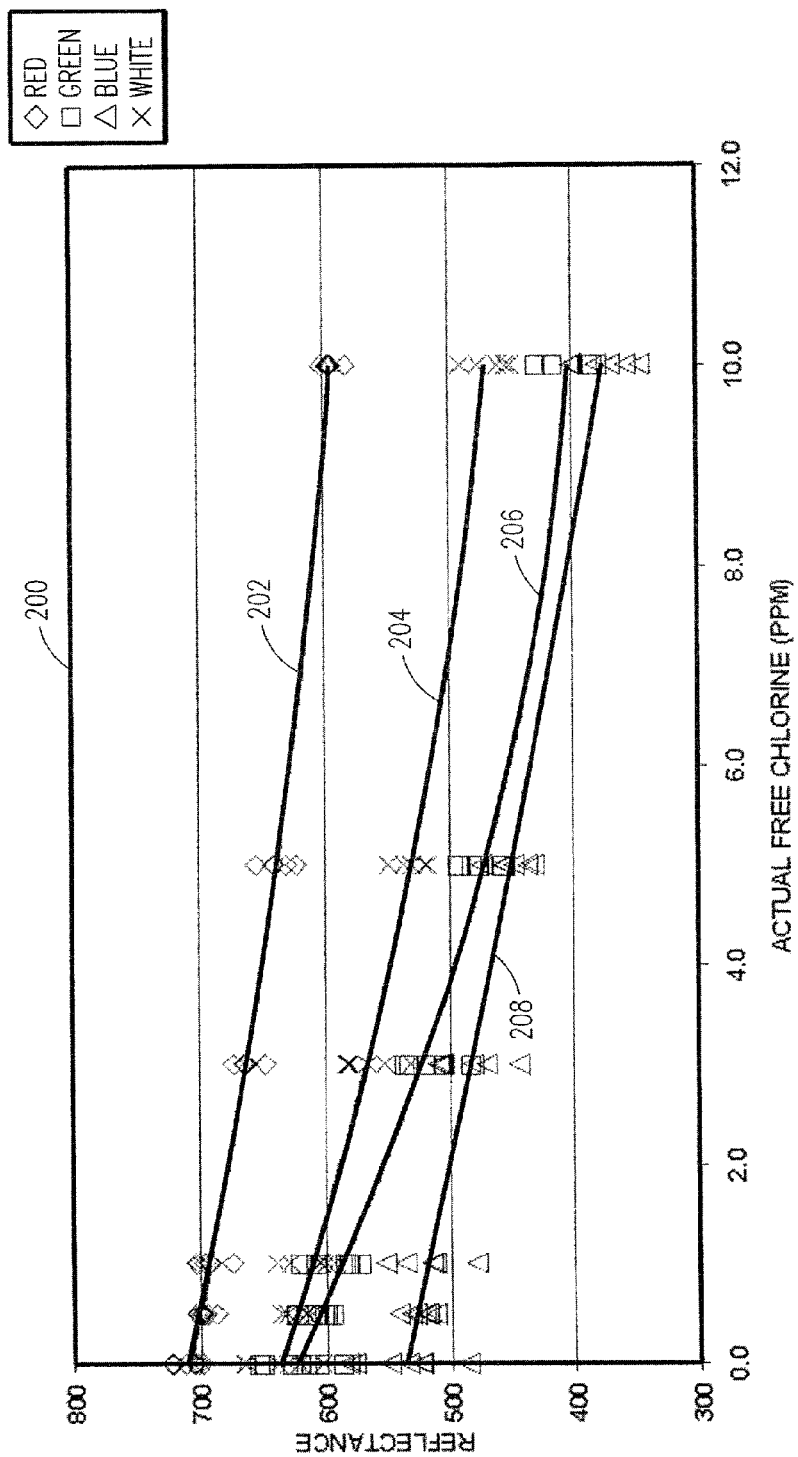
FIG. 9 is plot of reflectance values vs. free chlorine values illustrating a typical distribution of four color components of a free chlorine test portion of the test element of FIG. 1B over a range of free chlorine values as measured by the device of FIGS. 1A and 2-5.

Referring now to FIG. 9, a plot 200 is shown of reflectance values vs. actual free chlorine concentration for a number of control samples each having a different known free chlorine concentration value. The plot 200 illustrates the measurement signals produced by one of the radiation detection circuits described hereinabove in the form of Red, Green, Blue and White frequency components. The Red, or R, frequency component of the number of aqueous solution samples is represented by small diamonds having a curve 202 approximately fitted thereto. The White, or W, frequency component is illustrated by small x's having a curve 204 approximately fitted thereto. The Green, or G, frequency components are illustrated by small squares having a curve 206 approximately fitted thereto, and the Blue, or B, frequency components are represented by small triangles having a curve 208 approximately fitted thereto. In the plot 200 of FIG. 9, the R, G, B and W values represent ratios of frequency count values of the measured signals relative to a corresponding frequency count value of a calibration strip. Thus, for example, the R values represent ratios of measured R frequency values, in units of Hz, and an R frequency value, in units of Hz, of a calibration strip, e.g., a white calibration strip. The G, B and W values in the plot 200 of FIG. 9 represent similar ratios.

Figure 10:
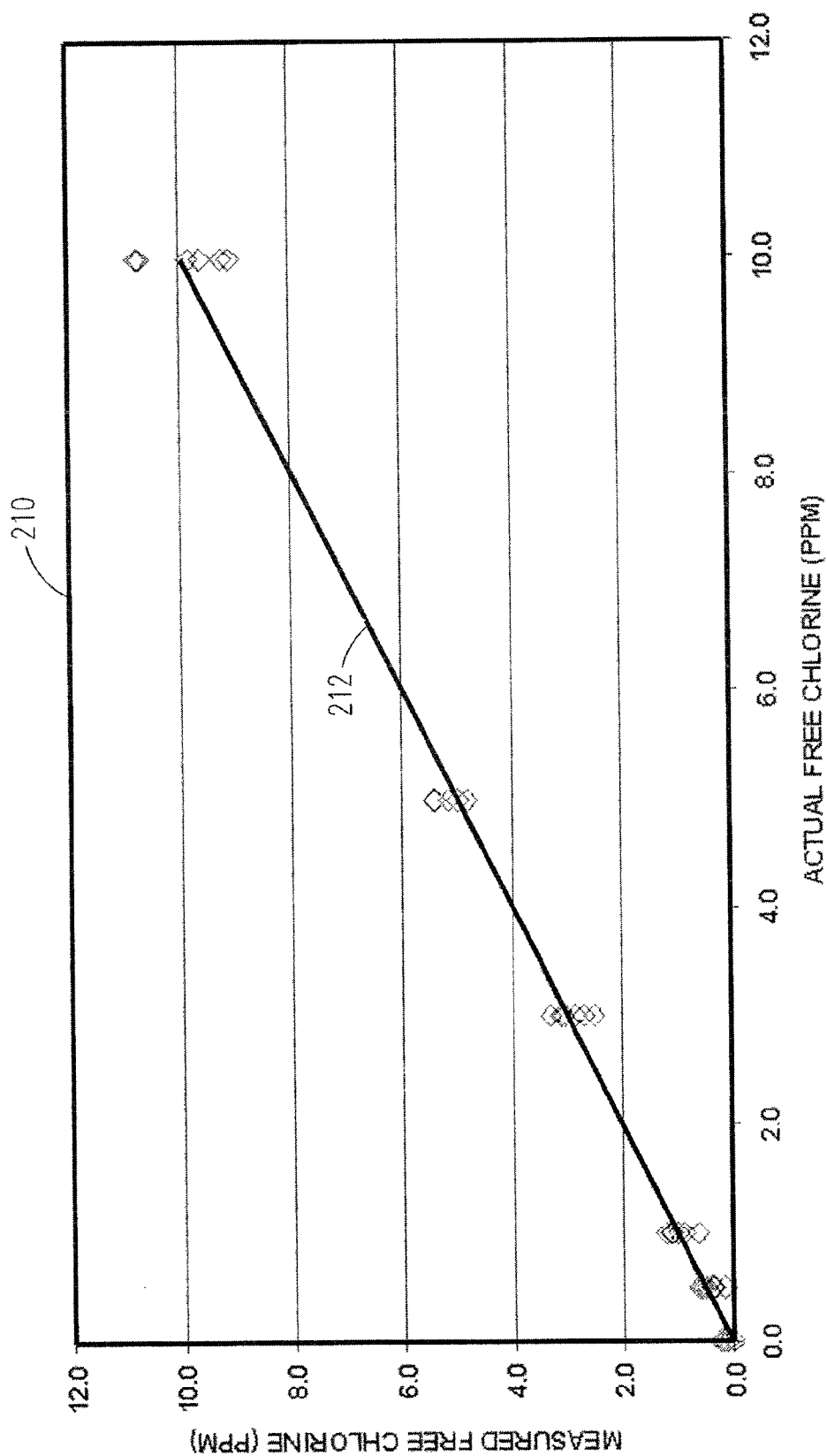
FIG. 10 is a plot of free chlorine values measured by the device of FIGS. 1A and 2-5 vs. actual free chlorine values of a number of aqueous solutions each having known chlorine concentration.

In the illustrated embodiment, the data in the plot 200 is used to form a 2-equation model for chlorine as a function of R, G, B and W. A first equation is of the form $ALG=(a*R+b*G+c*B+d*W)*R^e*G^f*B^g*W^h$, where a-h are constants. For the example data illustrated in FIG. 9, a=−0.281240, b=−1.454026, c=−0.20798, d=1.906914, e=−0.83526, $f=1.829174$, $g=-1.78626$ and $h=0.653039$. A second equation is of the form $MFCI=w*ALG^3+x*ALG^2+y*ALG+z$, where w-z are constants. For the example data illustrated in FIG. 9, $w=0.006304$, $x=-0.064922$, $y=0.422585$ and $z=0.483674$. In the operation of the system 10, the processor 102 is operable to process each set of R, G, B and W signals produced by the radiation detection circuit(s) according to the foregoing model to determine the free chlorine value of the aqueous solution to which the test element 16 has been exposed, and to display the result on the display unit 18. FIG. 10 is a plot 210 of the measured free chlorine values, MFCI, resulting from the free chlorine model, as measured by the device 10 of FIGS. 1A and 2-5, vs. the corresponding actual free chlorine values of the various aqueous solution control samples. The MFCI values are represented by small diamonds having a curve 212 approximately fitted thereto.

The first and second equations of the above free chlorine model define one embodiment of the free chlorine model that is stored in the memory unit 115. It will be understood that the forms of these first and second equations, as well as the example values of the various constants in these equations, are provided only for illustrative purposes, and alternate forms of the first and second equations and of any constants used therein are contemplated by this disclosure.

Figure 11:
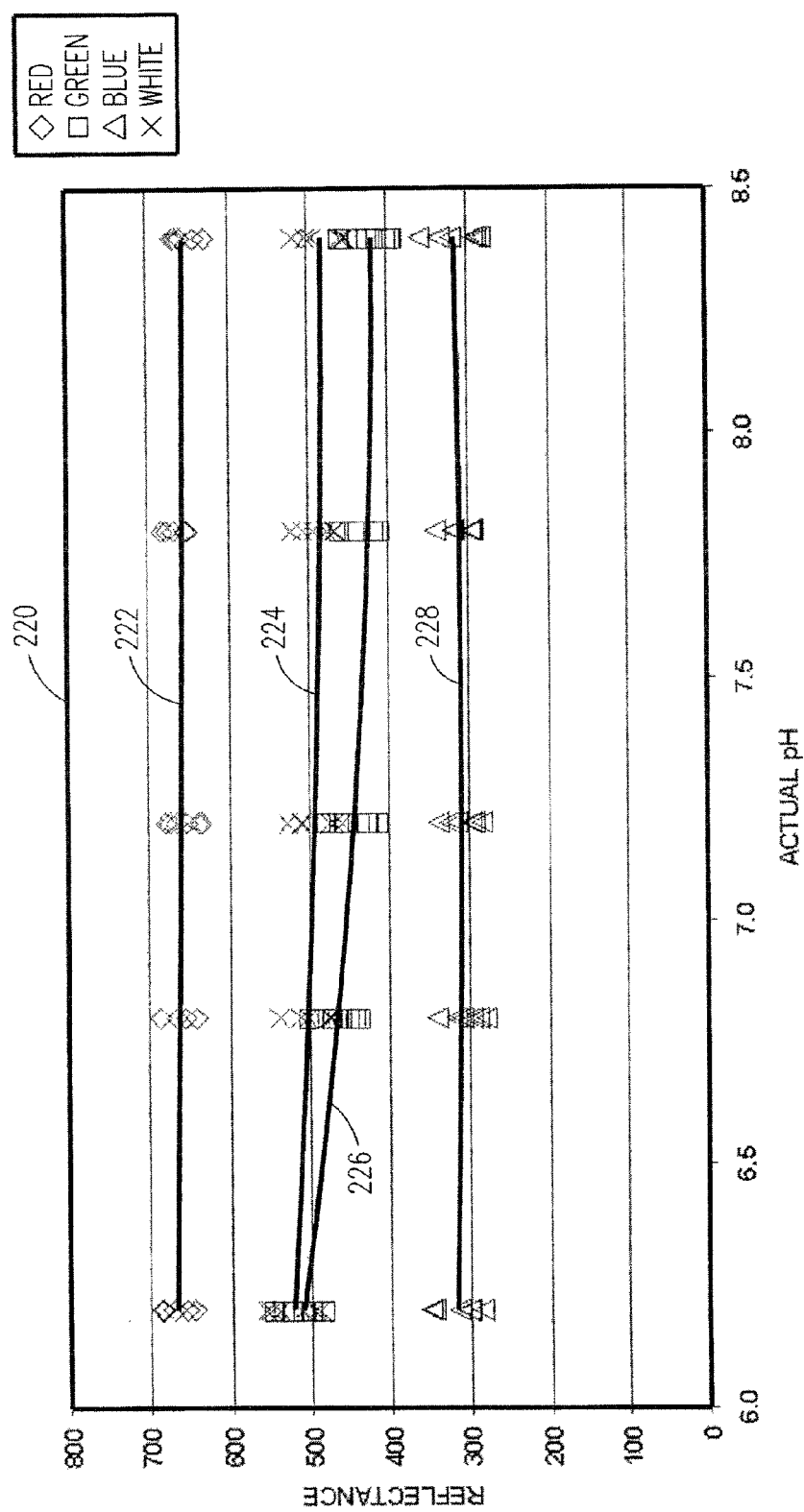
FIG. 11 is plot of reflectance values vs. relative pH values illustrating a typical distribution of four color components of a pH test portion of the test element of FIG. 1B over a range of relative pH values as measured by the device of FIGS. 1 and 3-5.

Referring now to FIG. 11, a plot 220 is shown of reflectance values vs. actual pH for a number of control samples each having a different known pH value. The plot 220 illustrates the measurement signals produced by one of the radiation detection circuits described hereinabove in the form of Red, Green, Blue and White frequency components. The Red, or R, frequency component of the number of aqueous solution samples is represented by small diamonds having a curve 222 approximately fitted thereto. The White, or W, frequency component is illustrated by small x's having a curve 224 approximately fitted thereto. The Green, or G, frequency components are illustrated by small squares having a curve 226 approximately fitted thereto, and the Blue, or B, frequency components are represented by small triangles having a curve 228 approximately fitted thereto. In the plot 220 of FIG. 11, the R, G, B and W values represent ratios of frequency count values of the measured signals relative to a corresponding frequency count value of a calibration strip, as described hereinabove with respect to FIG. 9.

Figure 12:
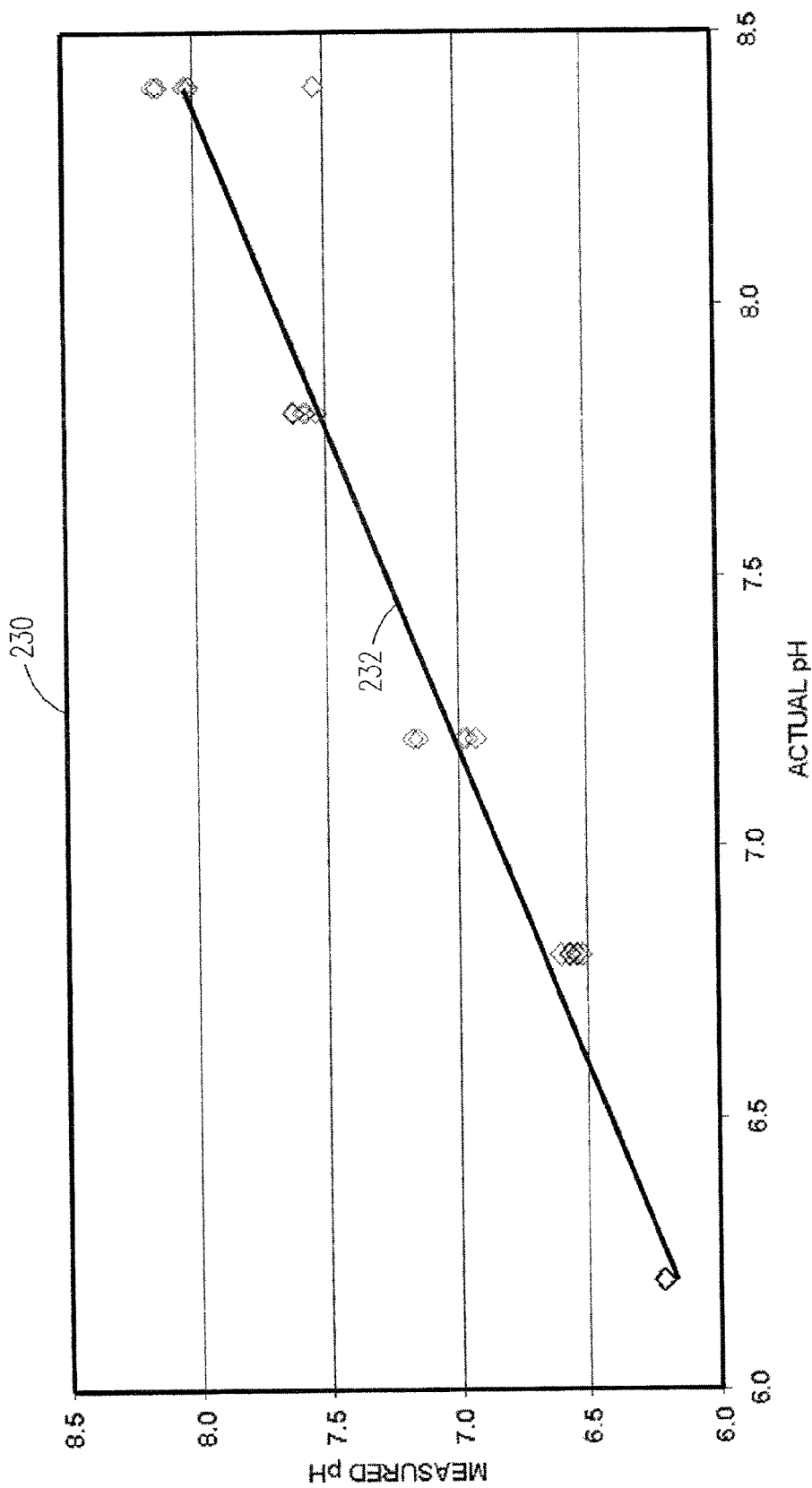
FIG. 12 is a plot of relative pH values measured by the device of FIGS. 1A and 2-5 vs. actual pH values of a number of controlled aqueous solutions each having known pH values.

In the illustrated embodiment, the data in the plot 220 is used to form a 2-equation model for pH as a function of R, G, B and W. A first equation is of the form $ALG=(a*R+b*G+c*B+d*W)*R^e*G^f*B^g*W^h$, where a-h are constants. For the example data illustrated in FIG. 11, $a=0.531448$, $b=-1.9864$, $c=1.20228$, $d=0.52574$, $e=-3$, $f=-2$, $g=2$ and $h=0.574138$. A second equation is of the form $MpH=w*(ALG*10^5)+x*(ALG*10^5)^2+y*(ALG*10^5)+z$, where w-z are constants. For the example data illustrated in FIG. 11, $w=-1.4315$, $x=3.0284$, $y=0.1661$ and $z=6.2109$. In the operation of the system 10, the processor 102 is operable to process each set of R, G, B and W signals produced by the radiation detection circuit(s) according to the foregoing model to determine the pH value of the aqueous solution to which the test element 16 has been exposed, and to display the result on the display unit 18. FIG. 12 is a plot 230 of the measured pH values, MpH, resulting from the pH model, as measured by the device 10 of FIGS. 1A and 2-5, vs. the corresponding actual pH values of the various aqueous solution control samples. The MpH values are represented by small diamonds having a curve 232 approximately fitted thereto.

The first and second equations of the above pH model define one embodiment of the pH model that is stored in the memory unit 115. It will be understood that the forms of these first and second equations, as well as the example values of the various constants in these equations, are provided only for illustrative purposes, and alternate forms of the first and second equations and of any constants used therein are contemplated by this disclosure.

Figure 13:
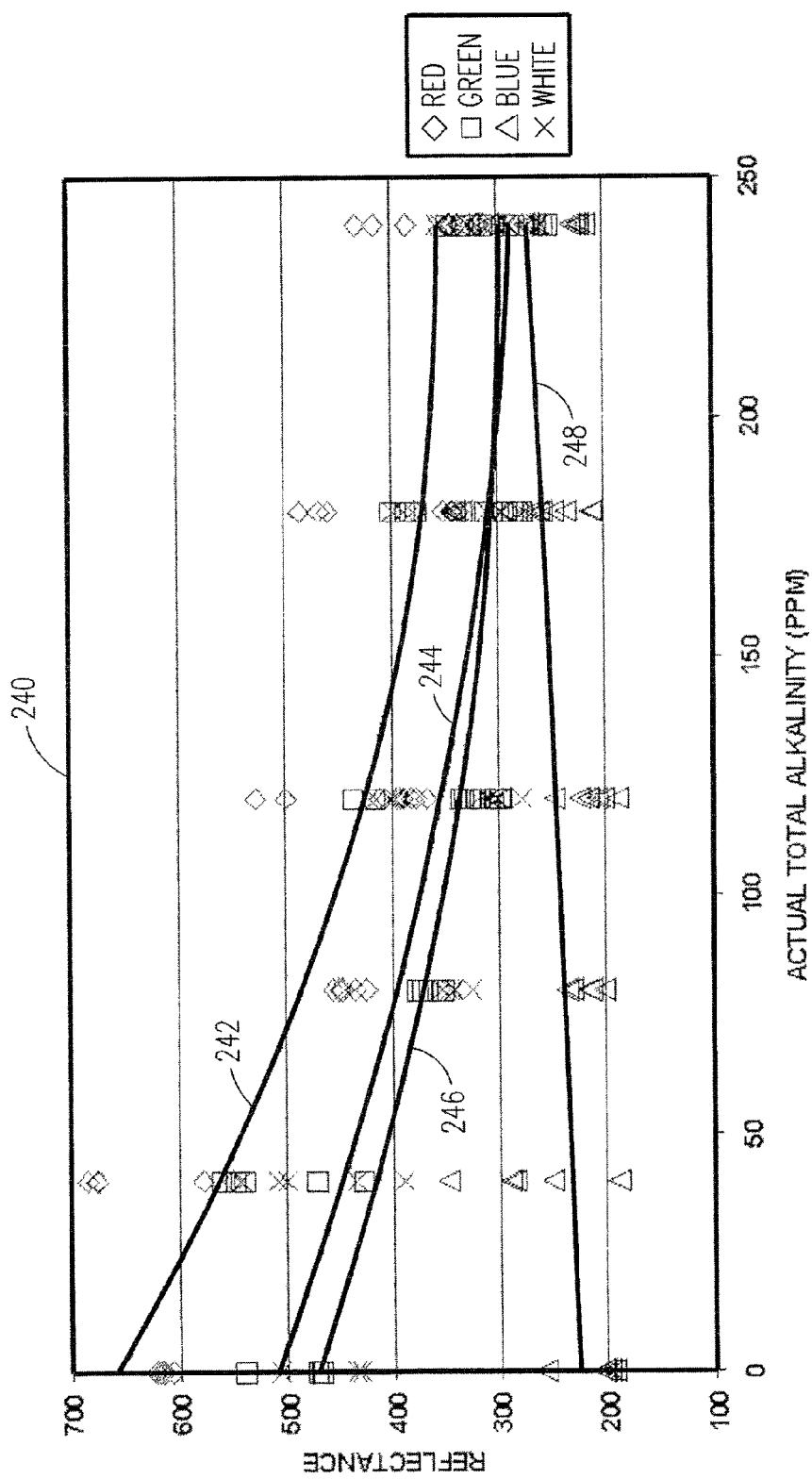
FIG. 13 is plot of reflectance values vs. total alkalinity values illustrating a typical distribution of four color components of an alkalinity test portion of the test element of FIG. 1B over a range of total alkalinity values as measured by the device of FIGS. 1A and 2-5.

Referring now to FIG. 13, a plot 240 is shown of reflectance values vs. actual total alkalinity for a number of control samples each having a different known alkalinity value. The plot 240 illustrates the measurement signals produced by one of the radiation detection circuits described hereinabove in the form of Red, Green, Blue and White frequency components. The Red, or R, frequency component of the number of aqueous solution samples is represented by small diamonds having a curve 242 approximately fitted thereto. The Green, or G, frequency component is illustrated by small squares having a curve 244 approximately fitted thereto. The white, or W, frequency components are illustrated by small x's having a curve 246 approximately fitted thereto, and the Blue, or B, frequency components are represented by small triangles having a curve 248 approximately fitted thereto. In the plot 240 of FIG. 13, the R, G, B and W values represent ratios of frequency count values of the measured signals relative to a corresponding frequency count value of a calibration strip, as described hereinabove with respect to FIG. 9.

Figure 14:
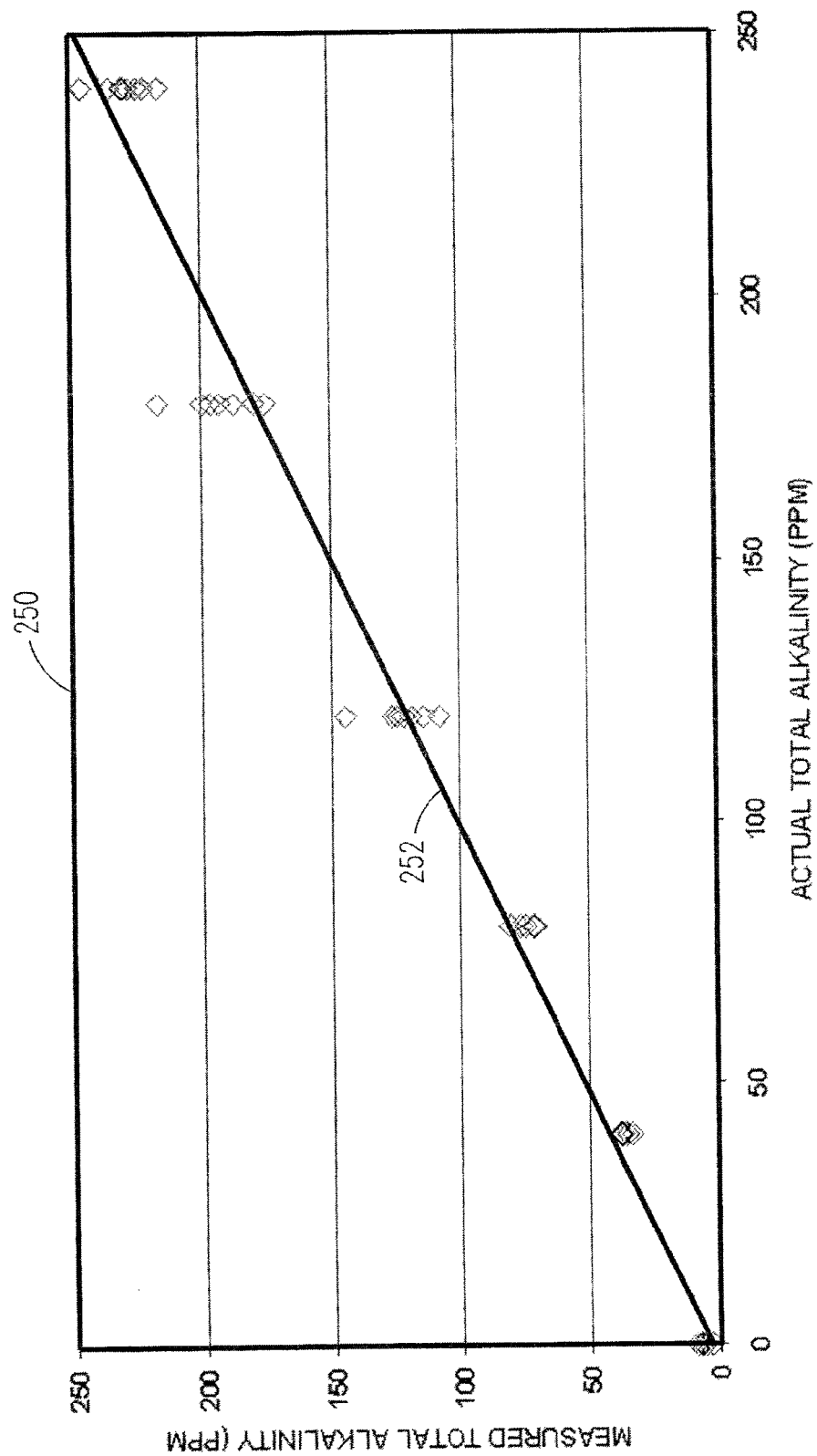
FIG. 14 is a plot of total alkalinity values measured by the device of FIGS. 1A and 2-5 vs. actual total alkalinity values of a number of aqueous solutions each having known total alkalinity values.

In the illustrated embodiment, the data in the plot 240 is used to form a 2-equation model for total alkalinity as a function of R, G, B and W. A first equation is of the form $ALG=(a*W+b*R+c*G+d*B)*W^e*R^f*G^g*B^h$, where a-h are constants. For the example data illustrated in FIG. 13, $a=-1.88019$, $b=0.202251$, $c=1.188813$, $d=-0.70284$, $e=-2.06506$, $f=-0.05257$, $g=1.885299$ and $h=-0.73126$. A second equation is of the form $MALK=x*ALG^2+y*ALG+z$, where x-z are constants. For the example data illustrated in FIG. 11, $x=-2367.2$, $y=-5822.9$ and $z=-3290.9$. In the operation of the system 10, the processor 102 is operable to process each set of R, G, B and W signals produced by the radiation detection circuit(s) according to the foregoing model to determine the total alkalinity value of the aqueous solution to which the test element 16 has been exposed, and to display the result on the display unit 18. FIG. 14 is a plot 250 of the measured total alkalinity values, MALK, resulting from the total alkalinity model, as measured by the device 10 of FIGS. 1A and 2-5, vs. the corresponding actual total alkalinity values of the various aqueous solution control samples. The MALK values are represented by small diamonds having a curve 252 approximately fitted thereto.

The first and second equations of the above pH model define one embodiment of the pH model that is stored in the memory unit 115. It will be understood that the forms of these first and second equations, as well as the example values of the various constants in these equations, are provided only for illustrative purposes, and alternate forms of the first and second equations and of any constants used therein are contemplated by this disclosure.

It is now possible, according to aspects of the present invention, to compensate for testing variables without the necessity for the interrogation of a pre-wetted test strip and subsequent adjustment of the power supplied to the LEDs, as is required in prior art U.S. Pat. No. 5,304,468 discussed above. Such testing variables may include variations in the intensity of the light produced by the radiation sources (LED's), variations in the degree of wetness of the test pad from test to test, dye leakage, etc. Prior art automatic blood and urine analyzers utilized only a single radiation frequency or narrow frequency band to obtain reflectance data, although a second frequency was known to be used to filter out blood color and chromatography effects due to varying hematocrit levels. Embodiments of the present invention may gather reflectance data in four wavelength ranges; i.e. frequencies generally described as red, green, blue and white, although the exact wavelength ranges and the detector responsivity may vary depending upon the specific detector circuitry used. For example, in one embodiment a red color range may include peak responsivity at about 690 nm and extending with reduced responsivity from about 600-800 nm; a green color range may include peak responsivity at about 540 nm and extending with reduced responsivity from about 450-625 nm; a blue color range may include peak responsivity at about 480 nm and extending with reduced responsivity from about 390-570 nm; and white color range may include peak responsivity at about 680 nm and extending with reduced responsivity across the entire visible spectrum and perhaps into the infrared ranges such as from about 300-800 nm. Collecting reflectance data across the spectrum in multiple wavelength ranges not only enables the analysis of multi-analyte solutions, but it also enables the calibration of the reflectance values as described above to account for process variables, thereby enabling the production of a self-calibrating electronic device 10 for analyzing various solutions. While the specific embodiment described above is provided for the purpose of illustration, one skilled in the art will appreciate that it is now possible on a more general basis to manipulate reflectance data gathered at a plurality of wavelength ranges to determine a characteristic of the analyzed solution without the necessity for separate radiation-intensity measuring and compensating steps. Reflectance values (e.g. counts) may be determined at the factory for each of a plurality of wavelength ranges (e.g. the red, green, blue and white ranges) when operating the electronic device 10 against both a white background ($R_{CW}$, $G_{CW}$, $B_{CW}$ and $W_{CW}$) and against a dark (black) background ($R_{CD}$, $G_{CD}$, $B_{CD}$ and $W_{CD}$). These values may be determined at the factory for each specific electronic device 10 or general values may be used to avoid the necessity for factory determination for each device. These values are then stored in a memory 115 as code (hardware or software or firmware) in the device 10. When an actual wefted test strip is interrogated, the reflectance values are obtained for each of the red ($R_t$), green ($G_t$), blue ($B_t$) and white ($W_t$) ranges and are converted to a relative reflectance value for each of the measured ranges (e.g. 0-100%) as follows:

$$R_{rel}=(R_t-R_{CD})/(R_{CW}-R_{CD})$$

$$G_{rel}=(G_t-G_{CD})/(G_{CW}-G_{CD})$$

$$B_{rel}=(B_t-B_{CD})/(B_{CW}-B_{CD})$$

$$W_{rel}=(W_t-W_{CD})/(W_{CW}-W_{CD})$$

These relative reflectance values are then manipulated in an algorithm to approximate the solution parameters. The algorithm functions to compare the intensity levels of each of the relative count values to each other to extract information regarding their relative values independent of the absolute reflectivity intensity values. For example, the ratio of intensity of red to green may vary as a function of the concentration of a analyte according to a first relationship; the ratio of intensity of green to blue may vary as a function of the concentration of the analyte according to a second relationship, the ratio of intensity of blue to white may vary as a function of the concentration of the analyte according to a third relationship, etc. These relationships will not be linear, so an algorithm used to devolve such relationships simultaneously for multiple frequency ranges will not be linear. An appropriate algorithm such as the ALG equations described above may be developed as a best fit to empirical data gathered over the analyte concentrations of interest by using techniques and software codes that are known and are commercially available, for example MATLAB® software by The Mathworks, Inc. The ALG values described above are unique numeric values or ratios that represent the measured analyte value, as converted into desired units by the M equations also described above. The coefficients of the algorithm are selected to provide a maximum difference in the calculated numeric value between different analyte concentration values.

It may be appreciated that ambient light will interfere with the accuracy and repeatability of the measurements obtained with any such optical instrument. Unlike prior art devices that rely upon removable caps or complicated shrouds for blocking ambient light, embodiments of the present invention may provide for the control of ambient light in a simple and cost effective manner. The test element receiving port 14 includes upwardly extending walls 14W that cooperate with the opaque/non-reflective material of the test strip substrate 28 to block ambient light and to control reflections during the interrogation of the test element 16 without the need for any separate overlying structure. The walls 14W may be disposed at right angles to the surface of the test element placement member 14B (i.e. vertical) or they may be sloped to form a tapered width that widens at the top to facilitate placement of the test strip while providing a small or essentially no gap along the edges of the test strip when it is in place on the test element placement member 14B. In one embodiment, a width of the opaque substrate 28 is no less than about 0.5 mm less than the distance between the opposed walls 14W of an associated tester 10 in order to minimize the amount of ambient light passing around the substrate 28 toward the test pads, yet allowing for manufacturing tolerances and for possible swelling of a water-soaked test pad. The gap between the sides of the substrate 28 and the walls 14W of the test element receiving port 14 is large enough to facilitate unobstructed placement of the test pads onto the test element placement member 14b while minimizing the area for stray light entry into the device 10. The test pads 30, 32, 34 are thus exposed to the interrogating radiation traveling through the transparent test element placement member 14B while being isolated from ambient light. Further, the side of the substrate attached to the test pads 30, 32, 34 may present a dark color, such as black, brown or gray for example, to be non-reflective in order to avoid optical color noise when the test element is illuminated by the LED 42.

Furthermore, opposed perimeter or edge portions 14E of the test element placement member 14B may be made effectively opaque, such as by being constructed of an opaque material or by being masked with an opaque coating, and may optionally wrap around the sides of the test strip 32 such as shown in FIG. 4. The walls 14W may abut the top of the upwardly turned sides of the edge portions 14E or they may extend downward along the inside surface of the edge portions 14E (not illustrated) to make contact with the same surface as the test pad 32. The walls 14W may be attached to the test element placement member 14B such as by ultrasonic welding. In this manner, the edge portions 32E of the test pad 32 and the opaque edge portion 14E of the test element placement member 14B and the opaque substrate 28 cooperate to provide a further barrier to the ingress of ambient light onto the more centrally located test portion 32T of the test pad 32 that is being interrogated by the radiation produced by radiation source 42. In one embodiment as illustrated in FIG. 4, a width of the opaque substrate 28 of the test element 16 is greater than a width of the transmissive central portion 14T of the test element placement member 14B, thereby requiring any intruding ambient light to traverse a serpentine path before it impinges on the interrogated surface or progresses into the transmissive portion 14T of the test element placement member 14B. Similarly, a length of the opaque substrate may be greater than a length of the transmissive central portion 14T of the test element placement member 14B so that an entire transmissive area 14A of the test element placement member 14B is effectively shielded from ambient radiation. An overall length of the test element 16 is longer than a length of the test element receiving port of the tester so as to project beyond the port to form an extension that can be gripped by a user to place the test element 16 into and out of the test element receiving port 14.

The placement of the test pad 32 against the test element placement member 14B, as illustrated in FIG. 4, provides the further advantage that it evens out variations in the reflectance that may result from variations in the degree of wetness of the test pad 32. Thus, the light reflected from the test pad 32 is more directly correlated to the color of the pad with less variation due to any gloss or matte effect resulting from degrees of wetness of the pad 32. Furthermore, any variation in the flatness of the test pad 32 due to manufacturing or handling problems, or due to swelling of the wetted pad material, does not change the optical distance between the surface being interrogated and the optics elements 42, 44, thereby eliminating such variations as a source of measurement error.

Based on the foregoing specification, the methods and functions described may be implemented using known computer programming or engineering techniques including computer software, firmware, hardware, circuitry or any combination or subset thereof. Any such resulting program, having computer-readable code means, may be embodied or provided within one or more computer-readable media, thereby making a computer program product, i.e., an article of manufacture, according to the invention. The computer readable media may be, for example, a fixed (hard) drive, diskette, optical disk, magnetic tape, semiconductor memory such as read-only memory (ROM), etc., or any transmitting/receiving medium such as the Internet or other communication network or link. The article of manufacture containing the computer code may be made and/or used by executing the code directly from one medium, by copying the code from one medium to another medium, or by transmitting the code over a network. One skilled in the art of computer science will be able to combine the software created as described with appropriate general purpose or special purpose computer hardware, such as a microprocessor, to create a computer system or computer sub-system embodying the method of the invention.

While the invention has been illustrated and described in detail in the foregoing drawings and description, the same is to be considered as illustrative and not restrictive in character, it being understood that only illustrative embodiments thereof have been shown and described and that all changes and modifications that come within the spirit of the invention are desired to be protected.

The invention claimed is:

1. A test element in combination with an associated electronic tester for determining a characteristic of an aqueous solution, the combination comprising:
the tester comprising a test element receiving port at least partially defined by a pair of opposed walls of a housing of the tester, with the walls extending upwardly from and juxtaposed about a test element placement member with at least a portion of the placement member being transparent to an interrogating radiation produced by the tester, the test element receiving port being attached to the opposed walls of the housing to create a seal isolating an interior of the housing from an exterior environment, including from aqueous solution on the test element, a source of the interrogating radiation disposed in the interior of the housing for illuminating the test element when positioned on the test element placement member, and a sensor disposed in the interior of the housing to detect interrogating radiation reflected from the illuminated test element, the test element comprising:
an opaque substrate;
a first side of the opaque substrate comprising a non-reflective surface; and
a test pad attached to the first side of the opaque substrate and comprising a reagent responsive in color to a characteristic of an aqueous solution and disposed to have a portion flattened against the test element placement member;
a radiation guide member disposed between the test element placement member and both the source of interrogating radiation and the sensor, the radiation guide member comprising a wall that does not transmit the interrogating radiation, with the radiation guide member at least partially defining a first passageway transmitting the interrogating radiation from the source of interrogating radiation to the flattened portion of the test pad and further defining a second passageway transmitting the reflected interrogating radiation from the flattened portion of the test pad to the sensor;
wherein the opaque substrate, the radiation guide wall and the non-reflective surface are configured to block transmission of ambient light to the sensor and to direct reflections of radiation from the test pad to the sensor during interrogation of the test pad by the tester when the test element is placed into the test element receiving port with the test pad disposed flat against the test element placement member.

2. The combination of claim 1, wherein the opaque substrate comprises a width larger than a width of the transparent portion of the test element placement member.

3. The combination of claim 1, wherein a width of the opaque substrate is at least about 0.5 mm greater than a distance between the opposed walls of the tester.

4. The combination of claim 1, wherein each of a width and a length of the opaque substrate is greater than a respective width and length of the transparent portion of the test element placement member of the tester so that an entire transmissive area of the test element placement member is effectively shielded from ambient light.

5. The combination of claim 1, wherein the substrate is black in color.

6. The combination of claim 1, wherein the substrate comprises black polystyrene.

7. The combination of claim 1, wherein a length of the test element is longer than a length of the test element receiving port of the tester so as to project beyond the port to form an extension configured to be gripped by a user.

8. The combination of claim 1 wherein the first side of the substrate presents a dark color to avoid optical color noise when the test element is illuminated by the source of radiation.

9. The combination of claim 1, further comprising a plurality of test pads affixed to the opaque substrate, each test pad comprising a respective reagent responsive in color to a respective different characteristic of the aqueous solution.

10. A test element and tester combination comprising:

a test element comprising a light-blocking opaque substrate, a test pad disposed on a first side of the opaque substrate and protected from ambient light impinging on an opposed second side of the opaque substrate, and a reagent on the test pad responsive to a characteristic of an aqueous solution to be tested; and a tester comprising a test element receiving port opening to an exterior of the tester for selectively receiving the test element, the test element receiving port being at least partially defined by a pair of opposed opaque walls of a housing of the tester extending upwardly from and juxtaposed about a transparent test element placement member, the transparent test element placement member being affixedly mounted on the housing so that aqueous solution within the test element receiving port on the exterior of the tester is sealed against entering an interior of the tester, a source of interrogating radiation in the interior of the tester for illuminating the test pad at a flattened portion when the test element is positioned in the test element receiving port with the test pad placed in face-to-face engagement with the test element placement member, with the transparent test element placement member being configured to engage and support the test pad in order to create and support the flattened portion of the test pad, and a sensor in the interior of the tester to detect radiation reflected from the illuminated flattened portion of the test pad;

the opaque substrate and the opaque walls configured to isolate the test pad from ambient light during illumination of the test pad with the interrogating radiation without the use of a cover over the test element receiving port.

11. The combination of claim 10 wherein the first side of the substrate comprises a non-reflective surface.

12. The combination of claim 10, wherein the opaque substrate comprises a width larger than a width of the transparent test element placement member.

13. The combination of claim 10, wherein a width of the opaque substrate is at least about 0.5 mm greater than a distance between opposed portions of the upwardly extending wall.

14. The combination of claim 10, wherein each of a width and a length of the opaque substrate is greater than a respective width and length of the transparent test element placement member so that an entire transmissive area of the test element placement member is effectively shielded from ambient light.

15. The combination of claim 10, wherein the substrate is black in color.

16. The combination of claim 10, wherein the substrate comprises black polystyrene.

17. The combination of claim 10, wherein a length of the test element is longer than a length of the test element receiving port so as to project beyond the port to form an extension configured to be gripped by a user.

18. The combination of claim 10 wherein the first side of the substrate comprises a dark color effective to avoid optical color noise when the test pad is illuminated by the interrogating radiation.

* * * * *